(12) United States Patent
Liu et al.

(10) Patent No.: US 11,633,424 B2
(45) Date of Patent: Apr. 25, 2023

(54) CELL PROTECTIVE METHODS AND COMPOSITIONS

(71) Applicant: The University of North Carolina at Chapel Hill, Chapel Hill, NC (US)

(72) Inventors: Jian Liu, Chapel Hill, NC (US); Jine Li, Chapel Hill, NC (US); Guowei Su, Chapel Hill, NC (US); Rafal Pawlinski, Chapel Hill, NC (US); Erica Sparkenbaugh, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 17/254,145

(22) PCT Filed: Jun. 19, 2019

(86) PCT No.: PCT/US2019/037993
§ 371 (c)(1),
(2) Date: Dec. 18, 2020

(87) PCT Pub. No.: WO2019/246264
PCT Pub. Date: Dec. 26, 2019

(65) Prior Publication Data
US 2021/0260098 A1 Aug. 26, 2021

Related U.S. Application Data

(60) Provisional application No. 62/687,540, filed on Jun. 20, 2018.

(51) Int. Cl.
*A61K 31/737* (2006.01)
*A61P 39/02* (2006.01)

(52) U.S. Cl.
CPC ............ *A61K 31/737* (2013.01); *A61P 39/02* (2018.01)

(58) Field of Classification Search
CPC .......... A61K 31/737; A61P 9/10; A61P 31/00; A61P 31/04
See application file for complete search history.

(56) References Cited

U.S. PATENT DOCUMENTS

| | | | |
|---|---|---|---|
| 4,554,101 A | 11/1985 | Hopp | |
| 4,865,870 A | 9/1989 | Hu et al. | |
| 5,543,403 A | 8/1996 | Petitou et al. | |
| 5,817,487 A | 10/1998 | Kobayashi et al. | |
| 5,834,282 A | 11/1998 | Habuchi et al. | |
| 5,935,824 A | 8/1999 | Sgarlato | |
| 6,255,088 B1 | 7/2001 | Wong et al. | |
| 6,861,254 B1 | 3/2005 | Rosenberg et al. | |
| 7,531,338 B2 | 5/2009 | Liu | |
| 9,951,149 B2 | 4/2018 | Liu et al. | |
| 10,286,047 B2 | 5/2019 | Spirig et al. | |
| 11,203,772 B2 | 12/2021 | Xu et al. | |
| 2003/0083294 A1 | 5/2003 | Sullenger | |
| 2003/0099967 A1 | 5/2003 | Deangelis | |
| 2004/0191870 A1 | 9/2004 | Rosenberg et al. | |
| 2005/0090601 A1 | 4/2005 | Dadalas et al. | |
| 2005/0090661 A1 | 4/2005 | Asari et al. | |
| 2005/0101532 A1 | 5/2005 | Yang et al. | |
| 2005/0191288 A1 | 9/2005 | Bennett et al. | |
| 2005/0255562 A1 | 11/2005 | Rosenberg et al. | |
| 2006/0165673 A1 | 7/2006 | Liu | |
| 2006/0172931 A1 | 8/2006 | San Antonio et al. | |
| 2006/0229276 A1* | 10/2006 | Hook .................... | A61K 31/737 514/56 |
| 2008/0109236 A1 | 5/2008 | DeAngelis | |
| 2009/0035787 A1 | 2/2009 | Liu | |
| 2009/0197308 A1 | 8/2009 | Liu | |
| 2010/0125052 A1 | 5/2010 | Lu et al. | |
| 2010/0298260 A1 | 11/2010 | Sundaram et al. | |
| 2010/0305022 A1 | 12/2010 | Shriver | |
| 2011/0054236 A1 | 3/2011 | Yang et al. | |
| 2012/0064044 A1 | 3/2012 | Egan | |
| 2012/0308546 A1 | 12/2012 | Kizhakkedathu et al. | |
| 2012/0322114 A1 | 12/2012 | Liu et al. | |

(Continued)

FOREIGN PATENT DOCUMENTS

| | | |
|---|---|---|
| CN | 105452479 B | 5/2021 |
| EP | 0 394 971 | 10/1990 |

(Continued)

OTHER PUBLICATIONS

Laremore, T. et al "Ionic liquid matrix for direct UV-MALDI-TOF-MS . . . " Anal. Chem., vol. 79, pp. 1604-1610. (Year: 2007).*
Belot, F. et al "Synthesis of chondroitin 4-and 6-sulfate pentasaccharide . . . " Carbohyd. Res., vol. 326, pp. 88-97. (Year: 2000).*
Li, J. et al "Enzymatic synthesis of homogeneous chondroitin sulfate oligosaccharides" Angew. Chem. Int. Ed., vol. 56, pp. 11784-11787. (Year: 2017).*
Advisory Action corresponding to U.S. Appl. No. 13/996,930 dated Dec. 9, 2016.
Aikawa et al., "Molecular Cloning and Expression of a Third Member of the Heparan Sulfate/Heparin GlcNAc N-Deacetylase/N-Sulfotransferase Family," The Journal of Biological Chemistry, vol. 274, No. 5, pp. 2690-2695 (Jan. 29, 1999).

(Continued)

*Primary Examiner* — Leigh C Maier
(74) *Attorney, Agent, or Firm* — Jenkins, Wilson, Taylor & Hunt, P.A.

(57) ABSTRACT

Chondroitin sulfate compounds comprising chondroitin sulfate backbone 19 mer, CS-A 19 mer, CS-C 19 mer, CS-E 19 mer, C8 backbone 13 mer, C8-A 13 mer, CS-C 13 mer, CS-E 13 mer and/or combinations thereof are provided. Methods of treating histone toxicity in a subject are provided, the methods including administering to a subject a chondroitin sulfate compound to treat the histone toxicity in the subject. Pharmaceutical compositions for use in treating histone toxicity and/or sepsis are provided. Methods of treating sepsis in a subject are provided, the methods including administering to a subject a chondroitin sulfate compound to treat the sepsis in the subject.

13 Claims, 10 Drawing Sheets

(56) References Cited

U.S. PATENT DOCUMENTS

| | | |
|---|---|---|
| 2012/0322760 A1 | 12/2012 | Fier et al. |
| 2013/0022647 A1 | 1/2013 | Kizhakkedathu et al. |
| 2013/0296540 A1 | 11/2013 | Xu et al. |
| 2013/0338097 A1* | 12/2013 | Stephens .............. A61K 31/727 514/61 |
| 2016/0122446 A1 | 5/2016 | Liu et al. |
| 2021/0137967 A1 | 5/2021 | Liu et al. |
| 2021/0169923 A1 | 6/2021 | Arnold et al. |
| 2022/0265699 A1 | 8/2022 | Arnold et al. |

FOREIGN PATENT DOCUMENTS

| | | |
|---|---|---|
| EP | 0 565 863 | 10/1993 |
| JP | 6670235 | 3/2020 |
| WO | WO 89/04328 | 5/1989 |
| WO | WO93/05167 | 3/1993 |
| WO | WO 96/14425 | 5/1996 |
| WO | WO2003018598 | 3/2003 |
| WO | WO 2004/005475 A2 | 1/2004 |
| WO | WO 2004/009642 | 1/2004 |
| WO | WO 2004/017910 A2 | 3/2004 |
| WO | WO 2006/124801 | 11/2006 |
| WO | WO 2012/088416 A2 | 6/2012 |
| WO | WO 2012/116048 | 8/2012 |
| WO | WO 2014/204929 | 12/2014 |
| WO | WO 2018/165656 | 9/2018 |
| WO | WO 2019/090203 A1 | 5/2019 |
| WO | WO 2021/097345 A1 | 5/2021 |

OTHER PUBLICATIONS

Aikawa et al., "Multiple Isozymes of Heparan Sulfate/Heparin GlcNAc N-Deacetylase/GlcN N-Sulfotransferase," The Journal of Biological Chemistry, vol. 276, No. 8, pp. 5876-5882 (Feb. 23, 2001).

Alexander et al., "Syndecan-1 is required for Wnt-1-induced mammary tumorigenesis in mice," Nat. Genet., vol. 25, pp. 329-332 (2000).

Altschul et al., "Basic Local Alignment Search Tool," J. Mol Bio., vol. 1215, pp. 403-410 (1990).

Antoine et al., "Mechanistic biomarkers provide early and sensitive detection of acetaminophen-induced acute liver injury at first presentation to hospital." Hepatology vol. 58, pp. 777-787 (2013).

Applicant-Initiated Interview Summary corresponding to U.S. Appl. No. 13/996,930 dated Jan. 23, 2017.

Arnold et al., "Design of anti-inflammatory heparan sulfate to protect against acetaminopheninduced acute liver failure." Sci. Transl. Med., vol. 12, Article ID eaav8075 (2020).

Arnold et al., "Synthetic anticoagulant heparan sulfate attenuates liver ischemia reperfusion injury." Sci. Reports, vol. 10, Article No. 17187 (10 pages) (2020).

Arungundram, S.; Al-Mafraji, K.; Asong, J.; Leach III, F. E.; Amster, I. J.; Venot, A.; JE, T.; Boons, G. J. "Modular Synthesis of Heparan Sulfate Oligosaccharides for Structure-Activity Relationship Studies," J. Am. Chem. Soc. 2009, 131, 17394.

Atha et al., "Contribution of Monosaccharide Residues in Heparin Binding to Antithrombin III," Biochemistry, vol. 24, pp. 6723-6729 (1985).

Avci et al., "Synthetic oligosaccharides as heparin-mimetics displaying anticoagulant properties," Curr. Pharm. Des., vol. 9, pp. 2323-2335 (2003).

Axelsson et al., "Inactivation of heparan sulfate 2-O-sulfotransferase accentuates neutrolphil infiltration during acute inflammation in mice." Blood. vol. 120, pp. 1742-1751 (2012).

Bailey et al., "Delays during the administration of acetylcysteine for the treatment of paraacetamol overdose." Br. J. Clin. Pharmacol. vol. 62, pp. 1358-1363 (2016).

Balagurunathan et al., Chemoenzymatic Synthesis of Classical and Non-classical Anticoagulant Heparan Sulfate Polysaccharide, J. Biol. Chem., vol. 278, pp. 52613-52621 (2003).

Balagurunathan et al., Enzymatic synthesis of antithrombin III-binding heparan sulfate pentasaccharide, Nat. Biotechnol., vol. 21, pp. 1343-1346 (2003).

Baleux et al. (2009) Nat. Chem. Biol., 5, 743-748.

Bernfield et al., "Heparin-Binding Proteins," Annu. Rev. Biochem., vol. 68, pp. 729-777 (1999).

Bianchi et al., "High-mobility group box 1 protein orchestrates responses to tissue damage via inflammation, innate and adaptive immunity, and tissue repair." Immunol. Rev. vol. 280, pp. 74-82 (2017).

Bitter et al. (1962) Anal. Biochem. 4, 330-334.

Bjornsson, Simultaneous Preparation and Quantitation of Proteoglycans by Preciptation with Alcian Blue, Anal. Biochem., vol. 210, pp. 282-291 (1993).

Blieden et al., "A perspective on the epidemiology of acetaminophen exposure and toxicity in the United States." Expert Rev. Clin. Pharmacol. vol. 7, pp. 341-348 (2014).

Bowman et al., Carbohydrate sulfotransferases: medliators of extracellular Communication, Chemistry & Biology, vol. 6, pp. R9-R22 (Jan. 1999).

Broun et al., "Catalytic plasticity of fatty acid modification enzymes underlying chemical diversity of plant lipids," Science, vol. 282, pp. 1315-1317 (1998).

Brown et al., Drug Research, "Cardenolide analogues. 11. Improved method for the use of Fetizon's reagent in the synthesis of cardiac glycosides", vol. 31, No. 7, pp. 1059-1064 (1981).

Burkart et al., "Regeneration of PAPS for the Enzymatic Synthesis of Sulfated Oligosaccharides," J. Org. Chem., vol. 65, pp. 5565-5574 (2000).

Cai et al., "Towards the chemoenzymatic synthesis of heparan sulfate oligosaccharides: Oxidative cleavage of p-nitrophenyl group with ceric ammonium salts," Tetra. Lett., vol. 54, No. 33, pp. 4471-1474 (2013).

Capila et al., "Heparin—Protein Interactions," Angew. Chem. Int. Ed., vol. 41, pp. 390-412 (2002).

Carfi et al., "Herpes Simplex Virus Glycoprotein D Bound to the Human Receptor HveA," Molecular Cell, vol. 8, pp. 169-179 (Jul. 2001).

Cassinelli et al., "Old and new applications of non-anticoagulant heparin." International Journal of Cardiology, 212S1 pp. S14-S21 (2016).

Casu et al., Heparin-like compounds prepared by chemical modification of capsular polysaccharide from *E. coli* K5, Carbohydrate Research vol. 263, pp. 271-28 (1994).

Chen et al., "Enzymatic redesigning of biologically active haparan sulfate," JBC, vol. 280, No. 52, pp. 42817-42825 (2005).

Chen et al., "Using an Enzymatic Combinatorial Approach to Identify Anticoagulant Heparan Sulfate Structures," Chemistry and Biology, Current Biology, London, GB, vol. 14., No. 9, pp. 986-993 (Sep. 19, 2007).

Chen et al., "Biosynthesis of 3-O-sulfated heparan sulfate: unique substrate specificity of heparan sulfate 3-O-sulfotransferase isoform 5," Glycobiology, vol. 13, No. 11, pp. 785-794 (Nov. 2003).

Chen et al., "Sterile inflammation: sensing and reacting to damage." Nat. Immunol. vol. 10, pp. 826-837 (2010).

Chen et al., Towards De Novo Synthesis of Structure-Defined Oligosaccharides with Heparan Sulfate Biosynthetic Enzymes, PhD dissertation,pp. 1-167. (Date Created: Aug. 2008; Date Deposited: Oct. 11, 2010.).

Chen et al., "Tyrosine-Ester Sulfotransferase from Rat Liver: Bacterial Expression and Identificationn," Protein Expression Purif., vol. 3, pp. 421-426 (1992).

Chen, M., et al. (2006) Biochemistry, 45, 12358-12365.

Clark SR, Ma AC, Tavener SA, McDonald B, Goodarzi Z, Kelly MM, et al. Platelet TLR4 activates neutrophil extracellular traps to ensnare bacteria in septic blood. Nat Med. 2007;13:463-9.

Communication of European publication number and information on the application of Article 67(3) EPC corresponding to European Application No. 14812890.3 dated Mar. 31, 2016.

Communication of the extended European search report corresponding to European Application No. 14812890.3 dated Dec. 21, 2016.

Conrad, Heparin-Binding Proteins, J. of Medicinal Chemistry, vol. 42, No. 4, pp. 777-778 (1998).

(56) References Cited

OTHER PUBLICATIONS

Copeland et al., "Using a 3-O-Sulfated Heparin Octasaccharide to Inhibit the Entry of Herpes Simplex Virus Type 1," Biochemistry, vol. 47, pp. 5774-5783 (2008).
Corrected Notice of Allowability corresponding to U.S. Appl. No. 16/492,858 dated Sep. 20, 2022.
Coutant et al., "2-Deoxy-2-trichloroacetamido-D-glucopyranose derivatives in oligosaccharide synthesis: from hyaluronic acid to chondroitin 4-sulfate trisaccharides" J Chem Soc Perkin Trans 1 (1995) 1573-1581 (Year: 1995).
Crowther et al., "Mechanisms responsible for the failure of protamine to inactivate low-molecular-weight heparin," British Journal of Hematology, vol. 116, pp. 178-186 (2002).
Darden, T.; York, D.; Pedersen, L. C. J. Chem. Phys. 1993, 98, 10089.
Das et al., "Synthesis of Conformationally Locked I-Iduronic Acid Derivatives: Direct Evidence for a Critical Role of the Skew-Boat 2S0 Conformer in the Activation of Antithrombin by Heparin," Chem. Eur. J., vol. 7, No. 22, pp. 4821-4834 (2001).
Davenport, "Review article: Low-molecular-weight heparin as an alternative anticoagulant to unfractionated heparin for routine outpatient haemodialysis treatments," Nephrology, vol. 14, pp. 456-461 (2009).
DeAgostini, A. I.; Dong, J.-C.; de Vantery Arrighi, C.; Ramus, M.-A.; Dentand-Quadri, I.; Thanlmann, S.; Ventura, P.; Ibecheole, V.; Monge, F.; Fischer, A.-M.; HajMohammadi, S.; Shworak, N.; Zhang, L.; Zhang, Z.; Linhardt , R. J. "Human Follicular Fluid Heparan Sulfate Contains Abundant 3-O-Sulfated Chains with Anticoagulant Activity," J. Biol. Chem. 2008, 283, 28115.
Decision to Grant corresponding to Japanese Patent Application No. 2016521505 dated Feb. 3, 2020.
Dementiev et al., "The ternary complex of antithrombin-anhydrothrombin-heparin reveals the basis of inhibitor specificity," Nat. Struct. Biol., vol. 11, pp. 867-863 (2004).
Dooley, T., "Cloning of the human phenol sulfotransferase gene family: three genes implicated in the metabolism of catecholamines, thyroid hormones and drugs," Chemico-Biological Interactions, vol. 109, pp. 29-41 (1998).
Dou et al., "Role of Deacetylase Activity of N-Deacetylase/N-Sulfotransferase 1 in Forming N-Sulfated Domain in Heparan Sulfate", The Journal of Biological Chemistry, vol. 290, No. 33, pp. 20427-20437 (Aug. 14, 2015).
Duncan et al., Biochim. Biophys. Acta, vol. 1671, pp. 34-43 (2004).
Edavettal et al.,, "Crystal Structure and Mutational Analysis of Heparan Sulfate 3-O-Sulfotransferase Isoform 1." J. Biol. Chem., vol. 279, No. 24, pp. 25789-25797 (Jun. 11, 2004).
Edens et al., "Gradient Polyacrylamide Gel Electrophoresis for Determination of Molecular Weights of Heparin Preparations and Low-Molecular-Weight Heparin Derivatives," J. Pharm. Sci., vol. 81, No. 8, pp. 823-827 (Aug. 1992).
Eller et al., "Automated Solid-Phase Synthesis of Chondroitin Sulfate Glycosaminoglycans." Angew. Chem. Int. Ed., vol. 52, pp. 5858-5861 (2013).
Esko et al., "Molecular diversity of heparan sulfate," J. Clin. Invest., vol. 108, pp. 169-173 (2001).
Esko et al., "Order Out of Chaos: Assembly of Ligand Binding Sites in Heparan Sulfate," Annu. Rev. Biochem., vol. 71, pp. 435-471 (2002).
European Search Report corresponding to European Patent Application No. 18764628.6 dated Dec. 2, 2020.
European Search Report corresponding to European Patent Application No. 18873131.9 dated Jul. 12, 2021.
Extended European Search Report Corresponding to European Patent Application No. 19822610.2 dated Mar. 29, 2022.
Falany, C., "Introduction: Changing view of sulfation and the cytosolic Sulfotransferases," vol. 11, The FASEB Journal, pp. 1-2 (Jan. 1997).
Feltracco et al., "Perioperative thrombotic complications in liver transplantation." World J. Gastroenterol., vol. 21, pp. 8004-8013 (2015).
Feng et al., "Characteristics Associated with Liver Graft Failure: The Concept of a Donor Risk Index." Am. J. Transplant., vol. 6, pp. 783-790 (2006).
Feyerabend et al., "Heparan sulfate C5-epimerase is essential for heparin biosynthesis in mast cells," Nat. Chem. Biol., vol. 2, No. 4, pp. 195-196 (Apr. 2006).
Fiser, A; Sali, A Methods Enzymol 2003, 374, 461.
Freeman et al., "The accumulation of circulating histones on heparan sulphate in the capillary glycocalyx of the lungs." Biomater., vol. 34, pp. 5670-5676 (2013).
Fried et al., "Designing a VAR2CSA-based vaccine to prevent placental malaria." Vaccine, vol. 33, pp. 7483-7488 (2015).
Fukuta et al., "Molecular cloning and expression of human chondroitin 6-sulfotransferase," Biochimica et Biophysica Acta, vol. 1399, pp. 57-61 (1998).
Fuster et al., The sweet and sour of cancer: glycans as novel therapeutic targets, Nat. Rev. Cancer, vol. 5, No. 7, pp. 1-27 (Jul. 2005).
Gallagher, "Heparan sulfate: growth control with a restricted sequence menu," J. Clin. Invest., vol. 108, pp. 357-361 (2001).
Gama et al., "Sulfation patterns of glycosaminoglycans encode molecular recognition and activity," Nat. Chem. Biol., vol. 2, No. 9, pp. 467-473 (Sep. 2006).
Ganey et al. "Role of the Coagulation System in Acetaminophen-Induced Hepatotoxicity in Mice." Hepatology, vol. 46(4), pp. 1177-1186 (2007).
Genbank Accession No. AAC40135 dated Jun. 17, 1998.
Genbank Accession No. BAA89247 dated Jan. 29, 2000.
Genbank Accession No. NP_005105 dated May 24, 2014.
Genbank Accession No. NP_006032 dated Feb. 26, 2014.
Genbank Accession No. NP_006033 dated Jan. 26, 2014.
Genbank Accession No. NP_056633 dated May 3, 2014.
Genbank Accession No. NP_056635 dated Mar. 3, 2014.
Gribskov,M., Burgess,R.R. and Devereux,J. (1986) Nucl. Acids Res. 14, 327-334.
Guerrini et al., "Oversulfated chondroitin sulfate is a contaminant in heparin associated with adverse clinical events," Nat. Biotechnol., vol. 26, No. 6, pp. 669-675 (Jun. 2008).
Guerrini, M.; Elli, S.; Mourier, P.; Rudd, T. R.; Gaudesi, D.; Casu, B.; Boudier, C.; Torri, G.; Viskov, C. "An unusual antithrombin-binding heparin octasaccharide with an additional 3-O-sulfated glucosamine in the active pentasaccharide sequence," Biochem. J. 2013, 449, 343.
Guerrini, M.; Mourier, P. A.; Torri, G.; Viskov, C. "Antithrombin-binding oligosaccharides: structural diversities in a unique function?," Glycoconj. J. 2014, 31, 409.
Guimond et al.,"Fibroblast growth factor receptor signaling is dictated by specific heparin sulphate saccharides," Curro. Biol., vol. 9, No. 22 pp. 1343-1346 (1999).
Guo et al., "Changes in substrate specificity of the recombinant form of phenol sulfotransferase IV (tyrosine-ester sulfotransferase)," Chem.-Biol. Interact., vol. 92, pp. 25-31 (1994).
Habuchi et al., The Occurrence of Three Isoforms of Heparan Sulfate 6-O-Sulfotransferase Having Different Specificities for Hexuronic Acid Adjacent to the Targeted N-Sulfoglucosamine, J. Biol. Chem., vol. 275, No. 4, pp. 2859-2868 (Jan. 28, 2000).
Habuchi et al., "Molecular Characterization and Expression of Heparan-sulfate 6-Sulfotransferase—Complete cDNA Cloning in Human and Partial Cloning in Chinese Hamster Ovary Cells," The Journal of Biological Chemistry, vol. 273, No. 15, pp. 9208-9213 (Apr. 10, 1998).
Habuchi et al., "Purification of Chondroitin 6-Sulfotransferase Secreted from Cultured Chick Embryo Chondrocytes," The Journal of Biological Chemistry, vol. 268(29), pp. 21968-21974 (1993).
HajMohammadi, S.; Enjyoji, K.; Princivalle, M.; Christi, P.; Lech, M.; Beeler, D. L.; Rayburn, H.; Schwartz, J. J.; Barzegar, S.; de Agostini, A. I.; Post, M. J.; Rosenberg, R. D.; Shworak, N. W. J. Clin. Invest. 2003, 111, 989.
Hansen, S. U.; Miller, G. J.; Cole, C.; Rushton, G.; Avizienyte, E.; Jayson, G. C.; Gardiner, J. M. Nat Commun 2013, 4:2016, doi:10.1038/ncomms3016.

(56) References Cited

OTHER PUBLICATIONS

Harada et al., "Dalteparin, a low molecular weight heparin, attenuates inflammatory responses and reduces ischemia-reperfusion-induced liver injury in rats." Crit. Care Med., vol. 34, Article No. 8, (2006).
Harris et al., Endocytic Function, Glycosaminoglycan Specificity, and Antibody Sensitivity of the Recombinant Human 190-kDa Hyaluronan Receptor for Endocytosis (Hare), J. Biol. Chem., vol. 279, No. 35, pp. 36201-36209 (Aug. 27, 2004).
Heard, "Acetylcystein for acetaminophen poisoning." N. Eng. J. Med. vol. 359, pp. 285-292 (2008).
Hernaiz et al., "Enzymatic Modification of Heparan Sulfate on a Biochip Promotes Its Interaction with Antithrombin III," Biochem. Biophys. Res. Commun., vol. 276, pp. 292-297 (2000).
Hirsch et al., Heparin and Low-Molecular-Weight Heparin The Seventh ACCP Conference on Antithrombotic and Thrombolytic Therapy, Chest, vol. 126, pp. 188S-203S (2004).
Hirsh et al., "Beyond Unfractionated Heparin and Warfarin Current and Future Advances," Circulation, vol. 116, pp. 552-560 (2007).
Holmborn et al., "Heparan Sulfate Synthesized by Mouse Embryonic Stem Cells Deficient in NDST1 and NDST2 is 6-O-Sulfated but Contains No N-Sulfate Groups," J. Biol. Chem., vol. 279, No. 41, pp. 42355-42358 (2004).
Hsieh et al., "Chemoenzymatic synthesis and structural characterization of 2-O-sulfated glucuronic acid containing heparan sulfate hexasaccharides." Glycobiology vol. 24, pp. 681-692 (2014).
Hsieh, P.-H.; Thieker, D. F.; Guerrini, M.; Woods, R. J.; Liu, J. Sci Rep 2016, 6, 29602; doi: 10.1038/srep29602.
Hu, Y.-P.; Lin, S.-Y.; Huang, C.-Y.; Zulueta, M. M. L.; Liu, J.-Y.; Chang, W.; Hung, S.-C. Nat Chem 2011, 3, 557.
Huang, C. C.; Meng, E. C.; Morris, J. H.; Pettersen, E. F.; Ferrin, T. E. Nucleic Acids Res. 2014, 42, w478.
Huebener el al., "The HMGB1/RAGE axis triggers neutrophil-mediated injury amplification following necrosis." J. Clin. Invest. vol. 125, pp. 539-550 (2015).
Humphrey, W.; Dalke, A; Schulten, K. J. Mol. Graph. 1996, 14, 33.
Iba et al., "Advance in the management of sepsis-induced coagulopathy and disseminated intravascular coagulation." J. Clin. Med., vol. 8, Article No. 728 (16 pages) (2019).
Ibrahimi et al., "Kinetic Model for FGF, FGFR, and Proteoglycan Signal Transduction Complex Assembly," Biochemistr, vol. 43, pp. 4724-4730 (2004).
Intention to Grant corresponding to European Patent Application No. 11849994.6 dated Apr. 7, 2021.
Intention to Grant corresponding to European Patent Application No. 11849994.6 dated Sep. 1, 2021.
Intention to Grant corresponding to European Patent Application No. 14812890.3 dated Oct. 27, 2021.
International Preliminary Report on Patentability corresponding to International Application No. PCT/US 2018/040774 dated Jan. 16, 2020.
International Preliminary Report on Patentability corresponding to International Application No. PCT/US2019/037993 dated Dec. 22, 2020.
International Preliminary Report on Patentability Corresponding to International Patent Application No. PCT/US 2020/060581 dated May 27, 2022.
International Preliminary Report on Patentability corresponding to International Application No. PCT/US2014/042683 dated Dec. 30, 2015.
International Preliminary Report on Patentability corresponding to International Application No. PCT/US2011/066843 dated Jul. 4, 2013.
International Preliminary Report on Patentability Corresponding to International application No. PCT/US 2018/021986 dated Sep. 19, 2019.
International Preliminary Report on Patentability corresponding to International application No. PCT/US 2018/059152 dated May 14, 2020.
International Search Report and the Written Opinion of the International Searching Authority Corresponding to International Application No. PCT/US 2018/040774 dated Sep. 18, 2018.
International Search Report and the Written Opinion of the International Searching Authority corresponding to International application No. PCT/US 2018/059152 dated Mar. 6, 2019.
International Search Report and Written Opinion of the International Searching Authority Corresponding to International Patent Application No. PCT/US 2020/060581 dated Feb. 11, 2021.
International Search Report and Written Opinion corresponding to International Application No. PCT/US2019/037993 dated Oct. 18, 2019.
International Search Report and Written Opinion corresponding to International Application No. PCT/US2014/042683 dated Oct. 9, 2014.
International Search Report and Written Opinion Corresponding to International application No. PCT/US 2018/021986 dated Aug. 1, 2018.
Jackson et al., "Thromboinflammation: challenges of therapeutically targeting coagulation and other host defense mechanisms." Blood, vol. 133, pp. 906-918 (2019).
Jaeschke et al., "Complement activates Kupffer cells and neutrophils during reperfusion after hepatic ischemia." Am. J. Physiol-Gastroint. Liver Physiol., vol. 264, pp. G801-G809 (1993).
Jaimes et al., "Unfractioned heparin for treatment of sepsis: A randomized clinical trial (The HETRASE Study)." Crit. Care Med., vol. 37, pp. 1185-1196 (2009).
Jemth et al., "Oligosaccharide library-based assessment of heparan sulfate 6-0-sulfotransferase substrate specificity," Journal of Biological Chemistry, vol. 278, No. 27, pp. 24371-24376 (Jul. 4, 2003).
Jin, L.; Abrahams, P.; Skinner, R.; Petitou, M.; Pike, R. N.; Carrell, R. W. Proc. Natl. Acad. Sci. 1997, 94, 14683.
Kakkar et al., "Low Molecular Weight Heparin, Therapy With Dalteparin, and Survival in Advanced Cancer: The Fragmin Advanced Malignancy Outcome Study (FAMOUS)," J. Clin. Oncol., vol. 22, No. 10, pp. 1944-1948 (May 15, 2004).
Kakuta et al., "Heparan sulphate N-sulphotransferase activity: reaction mechanism and substrate recognition," Biochem. Soc. Trans., vol. 31 (pt2), pp. 331-334 (2003).
Kamimura, K.; Rhodes, J. M.; Ueda, R.; McNeely, M.; Shukla, D.; Kimata, K.; Spear, P. G.; Shworak, N. W.: Nakata, H. J. Cell Biol. 2004, 166, 1069.
Kaneko et al., "Coagulation and fibrinolytic profiles and appropriate use of heparin after living-donor liver transplantation." Clin. Transplant., vol. 19, pp. 804-809 (2005).
Kirschner, K. N.; Yongye, A B.; Tschampel, S. M.; Gonzalez-Outeirino, J.; Daniels, C. R.; Foley, B. L.; Woods, R. J. J. Comput. Chem. 2008, 29, 622.
Kisselev, L., "Polypeptide release factors in prokaryotes and eukaryotes: same function, different structure," Structure, vol. 10, pp. 8-9 (2002).
Kollman, P. A; Massova, I.; Reyes, C.; Kuhn, B.; Hua, S.; Chong, L.; Lee, M.; Lee, T.; Duan, Y.; Wang, W.; Donini, O.; Cieplak, P.; Srinivasan, J.; Case, D. A; Cheatham, T. E. r. Acc. Chem. Res. 2000, 33, 889.
Konishi et al., "Hepatic ischemia/reperfusion: mechanisms of tissue injury, repair, and regeneration." Gene Expr., vol. 17, pp. 277-287 (2017).
Kopec et al., "Fibrin(ogen) drives repair after acetaminophen-induced liver injury via leukocyte aMb2 integrin-dependent upregulation of Mmp12." J. Hepatol. vol. 66, pp. 787-797 (2017).
Kreimann, M.; Brandt, S.; Krauel, K.; Block, S.; Helm, C.; Weitschies, W.; Greinacher, A.; Delcea, M. Blood 2014, in press.
Kreuger et al., Interactions between heparan sulfate and proteins: the concept of specificity, J. Cell Biol., vol. 174, No. 3, pp. 323-327 (Jul. 31, 2006).
Krummenacher et al., "The First Immunoglobulin-Like Domain of HveC is Sufficient to Bind Herpes Simplex Virus gD with Full Affinity, While the Third Domain is Involved in Oligomerization of HveC," J. Virol., vol. 73, pp. 8127-8137 (Oct. 1999).
Kuberan et al., "Enzymatic synthesis of antithrombin III-binding heparan sulfate pentasaccharide," Nature Biotechnology, vol. 21, No. 11, 1343-1346 (Nov. 2003).

(56) References Cited

OTHER PUBLICATIONS

Kuberan et al., "Rapid Two-Step Synthesis of Mitrin from Heparosan: A Replacement for Heparin," J. Am. Chem. Soc., vol. 125, pp. 12424-12425 (2003).
Kuberan. et al., The Journal of Biological Chemistry, "Chemoenzymatic Synthesis of Classic and Non-classical Anticoagulant Heparan Sulfate Polysaccharides", 2003, vol. 278, No. 52, pp. 52613-52621 (Year: 2003).
Kubes et al., "Sterile inflammation in the liver." Gastroenterology, vol. 143, pp. 1158-1172 (2012).
Kyte & Doolittle (1982) A Simple Method for Displaying the Hydropathic Character of a Protein. J. Mol Biol,157: 105-132.
Langdown, J.; Belzar, K. J.; Savory, W. J.; Baglin, T. P.; Huntington, J. A. J. Mo/. Biol. 2009, 386, 1278.
Laremore, T. et al "Ionic liquid matrix for direct UV-MALDI-TOF-MS Analysis of Dermatan Sulfate and Chondroitin Sulfate Oligosaccharides." Anal. Chem., vol. 79, pp. 1604-1610. (Year: 2007).
Laurent et al., "The Molecular-Weight-Dependence of the Anti-Coagulant Activity of Heparin," Biochem. J., vol. 175, pp. 691-701 (1978).
Ledin et al., "Heparan Sulfate Structure in Mice with Genetically Modified Heparan Sulfate Production," J. Biol. Chem., vol. 279, No. 41, pp. 42732-42741 (2004).
Lee, "Acetaminophen toxicity: changing perceptions on a social/medical issue." Hepatology, vol. 46, pp. 966-970 (2007).
Lee, M.K., and Lander, A.D., (1991) Proc. Natl. Acad. Sci. USA 88, 2768-2772.
Li et al., "Biosynthesis of Heparin/Heparan Sulfate cDNA Cloning and Expression of D-Glucuronyl C5-Epimerase From Bovine Lung," J. Biol. Chem., vol. 272, No. 4, pp. 28158-28163 (Oct. 31, 1997).
Li et al., "Enzymatic synthesis of homogenous chondroitin sulfate e oligosaccharides." Glycobiol., vol. 28(12) (2018).
Li J, Su W, and Liu J. "Enzymatic synthesis of homogeneous chondroitin sulfate oligosaccharides." Angew Chem Int Ed. 2017;56:11784-7.
Liliensiek et al., "Receptor for advanced glycation end products (RAGE) regulates sepsis but not the adaptive immune response." J. Clin. Invest. vol. 113, pp. 1641-1650 (2004).
Lin et al., "Colorimetric Determination of the Purity of 39-Phospho Adenosine 59-Phosphosulfate and Natural Abundance of 39-Phospho Adenosine 59-Phosphate at Picomole Quantities," Anal. Biochem., vol. 264. pp. 111-117 (1998).
Lin et al., "Enzymatic Synthesis and Regeneration of 3'-Phosphoadenosine 5'Phosphosulfate (PAPS) for Regioselective Sulfation of Oligosaccharides," J. Am. Chem. So., vol. 117, pp. 8031-8032 (1995).
Lindahl et al., "Regulated Diversity of Heparan Sulfate," The Journal of Biological Chemistry, vol. 273, No. 39, pp. 24979-24982 (Sep. 25, 1998).
Lindahl et al., "Generation of "Neoheparin" from E. coli K5 Capsular Polysaccharide," J. Med. Chem., vol. 48, pp. 349-352 (2005).
Lindahl, U.; Backstrom, G.; Thunberg, L.; Leder, I. G. Proc. Natl. Acad. Sci. 1980, 77, 6551.
Linhardt et al., "Production and Chemical Processing of Low Molecular WQeight Heparins," Seminars in Thrombosis and Hemostasis, vol. 25, Suppl.3, pp. 5-16 (1999).
Linhardt, R. J., J. Med. Chem., vol. 46, pp. 2551-2564 (2003).
Liu et al., "Anticoagulant heparan sulfate: structural specificity and biosynthesis," Appl Microbiol Biotechnol., vol. 74, pp. 263-272 (2007).
Liu et al., "Cell Surface Heparan Sulfate and Its Roles in AssistingViral Infections," Medicinal Research Reviews, vol. 22, No. 1, pp. 1-25 (2002).
Liu et al., "Characterization of a Heparan Sulfate Octasaccharide that Binds to Herpes Simplex Virus Type 1 Glycoprotein D," The Journal of Biological Chemistry, vol. 277, No. 36, pp. 33456-33467 (Sep. 6, 2002).

Liu et al., "Expression of Heparan Sulfate D-Glucosaminyl 3-O-Sulfotransferase Isoforms Reveals Novel Substrate Specificities," The Journal of Biological Chemistry, vol. 274, No. 8, pp. 5185-5192 (Feb. 19, 1999).
Liu et al., "Heparan Sulfate D-Glucosaminyl 3-O-Sulfotransferase-3A Sulfates N-Unsubstituted Glucosamine Residues," The Journal of Biological Chemistry vol. 274, No. 53, pp. 38155-38162 (Dec. 31, 1999).
Liu et al., "Purification of Heparan Sulfate D-Glucosaminyl 3-O-Sulfotransferase," The Journal of Biological Chemistry, vol. 271, No. 43, pp. 27072-27082 (Oct. 25, 1996).
Liu et al., Chemoenzymatic Design of Heparan Sulfate Oligosaccharides, J Biol Chem, vol. 285, No. 44, pp. 34240-34249 (Oct. 29, 2010).
Liu et al., "Enzymatic Placement of 6-O-Sulfo Groups in Heparan Sulfate," Biochemistry 2011, 50, 4382-4391.
Liu et al., "Lessons learned from the contamination of heparin," Nat. Prod. Rep., vol. 26, pp. 313-321 (2009).
Liu, J. et al., Royal Society of Chemistry, "Chemoenzymatic synthesis of heparan sulfate and heparin", vol. 31, pp. 1676-1685 (Year: 2014).
Loganathan et al., "Structural Variation in the Antithrombin III Binding Site Region and Its Occurrence in Heparin from Different Sources," Biochemistry, vol. 29, pp. 4362-4368 (1990).
Lopin et al., "From Polymer to Size-Defined Oligomers: An Expeditious Route for the Preparation of Chondroitin Oligosaccharides." Angew. Chem. Int. Ed., vol. 45, pp. 2574-2578 (2006).
Lopin-Bon et al., "Stereocontrolled preparation of biotinylated chondroitin sulfate E di-, tetra-, and hexasaccharide conjugates." Carbohydr. Res., vol. 402, pp. 35-43 (2015).
Lu et al., "Innate Immune Regulations and Liver Ischemia-Reperfusion Injury." Trasplantation, vol. 100, pp. 2601-2610 (2016).
Lundbäck et al., "A novel high mobility group box 1 neutralizing chimeric antibody attenuates drug-induced liver injury and postinjury inflammation in mice." Hepatology vol. 64, pp. 1699-1710 (2016).
Ly et al., "The proteoglycan bikunin has a defined sequence." Nat. Chem. Biol., vol. 7, pp. 827-833 (2011).
Maccarana et al., J. Biol. Chem., vol. 268, pp. 23898-23905 (1993).
Macchione et al., "Synthesis of chondroitin sulfate oligosaccharides using N-tetrachlorophthaloyl and N-trifluoroacetyl galactosamine building blocks," European Journal of Organic Chemistry, pp. 3868-3884 (2014).
Mackman, "Triggers, targets and treatments for thrombosis," Nature, vol. 451, No. 21, pp. 914-918 (Feb. 21, 2008).
Mahe, I.; Chidac, J.; Helfer, H.; Nobel, S. J. Thromb. Haemost. 2016, 14, 2107.
Man et al., "Tolerance of the liver to intermittent pringle maneuver in hepatectomy for liver tumors." JAMA Sirgery, vol. 134, pp. 533-539 (1999).
Marcus et al. Anal. Biochem., vol. 107, pp. 296-304 (1980).
Marshall et al., "A review of the effects of manipulation of the cysteine residues of rat aryl sulfotransferase IV," Chem. Biol. Interact., vol. 109, pp. 107-116 (1998).
Marshall et al., "Control of Activity through Oxidative Modification at the Conserved Residue Cys66 of Aryl Sulfotransferase IV," J. Biol. Chem., vol. 272, No. 14, pp. 9153-9160 (Apr. 14, 1997).
Martinez-Gonzalez et al., "New Challenges for a Second-Generation Low-Molecular-Weight Heparin: Focus on Bemiparin," Expert Rev. Cardiovasc. Ther., vol. 8, No. 5, pp. 625-634 (2010).
Mazany et al., "Human chondroitin 6-sulfotransferase: cloning, gene structure, and chromosomal localization," Biochimica et Biophysica Acta, vol. 1407, pp. 92-97 (1998).
McGowan, K. E.; Makari, J.; Diamantouros, A.; Bucci, C.; Rempel, P.; Selby, R.; Geerts, W. Blood 2016, 127, 1954.
Miyachi et al., "Syntheses of chondroitin sulfate tetrasaccharide structures containing 4,6-disulfate patterns and analysis of their interaction with glycosaminoglycan-binding protein." Bioorg. Med. Chem. Lett, vol. 25, pp. 1552-1555 (2015).
Miyata et al., "Persistent cortical plasticity by upregulation of chondroitin 6-sulfation." Nat. Neurosci., vol. 15, pp. 414-422 (2012).
Mizumoto et al., "Molecular interactions between chondroitin-dermatan sulfate and growth factors/receptors/matrixproteins." Curr. Opin. Struct. Biol., vol. 34, pp. 35-42 (2015).

(56) References Cited

OTHER PUBLICATIONS

Monneau et al., "The sweet spot: how GAGs help chemokines guide migrating cells." J. Leukoc. Biol. vol. 99, pp. 935-953 (2016).
Moon et al., "Dissecting the substrate recognition of 3-O-suflotransferase for the biosynthesis of anticoagulant heparin," Proceedings of the National Academy of Sciences, vol. 109, No. 14, pp. 5265-5270 (2012).
Moon et al., "Structural Analysis of the Sulfotransferase (3-O-Sulfotransferase Isoform 3) Involved in the Biosynthesis of an Entry Receptor for Herpes Simplex Virus 1," J. Biol. Chem., vol. 279, No. 43, pp. 45185-45193 (2004).
Mossanen et al., "Acetaminophen-induced acute liver injury in mice." Lab. Anim. vol. 49, pp. 30-36 (2015).
Mousa, "Drug Discovery and Evaluation: Pharmacological Assays" (ed. Vogel, H.), 393-456 (Springer-Verlag Berlin, Heidelberg, New York (2008).
Mousa, "Heparin and Low-Molecular Weight Heparins in Thrombosis and Beyond," Meth. Mol. Biol., vol. 663, pp. 109-132 (2010).
Mousa, "In Vitro Methods of Evaluating Antithrombotics and Thrombolytics," Meth. Mol. Biol., vol. 663, pp. 1-28 (2010).
Munoz et al., "Enzymatic synthesis of heparin related polysaccharides on sensor chips: Rapid screening of heparin-protein interactions," Biochemical and Biophysical Research Communications, Academic Press Inc., Orlando, FL, US, vol. 339, No. 2, pp. 597-602 (Jan. 13, 2006).
Nadanaka et al., "Characteristic Hexasaccharide Sequences in Octasaccharides Derived from Shark Cartilage Chondroitin Sulfate D with a Neurite Outgrowth Promoting Activity," The Journal of Biological Chemistry, vol. 273(6), pp. 3296-3307 (1998).
Nagano et al., "Chondroitin sulfate protects vascular endothelial cells from toxicities of extracellular histones." Eur. J. Pharmacol., vol. 826, pp. 48-55 (2018).
Nam et al., "Syndecan-1 Limits the Progression of Liver Injury and Promotes Liver Repair in Acetaminophen-Induced Liver Injury in Mice." Hepatology, vol. 66(5), pp. 1601-1615, doi: 10.1002/hep.29265 (2017).
Nastuk et al., "Expression Cloning and Characterization of NSIST, a Novel Sulfotransferase Expressed by a Subset of Neurons and Postsynaptic Targets," The Journal of Neuroscience, vol. 18, No. 18, pp. 7167-7177 (Sep. 15, 1998).
Needleman et al., "A General Method Applicable to the Search for Similarities in the Amino Acid Sequence of Two Proteins," J. Mol. Biol., vol. 48, pp. 443-453 (1970).
Nicola et al., Structure-Function Analysis of Soluble Forms of Herpes Simplex Virus Glycoprotein D., J. Virol., vol. 70, No. 6, pp. 3815-3822 (1996).
Noti et al., "Chemical Approaches to Define the Review Structure-Activity Relationship of Heparin-like Glycosaminoglycans," Chemistry & Biology, vol. 12, pp. 731-756 (Jul. 2005).
Notice of Allowance and Interview Summary corresponding to U.S. Appl. No. 14/898,865 dated Dec. 15, 2017.
Notice of Allowance corresponding to U.S. Appl. No. 16/492,858 dated Sep. 12, 2022.
Notice of Allowance corresponding to U.S. Appl. No. 13/996,930 dated Aug. 11, 2021.
Notice of Issuance corresponding to Chinese Patent Application No. 201480044429.9 dated May 7, 2021.
Notice of Publication Corresponding to European Patent Application. No. 19822610.2 dated Mar. 31, 2021.
Notice of Publication of Application Corresponding to U.S. Appl. No. 16/625,342 dated Oct. 28, 2021.
Notification Concerning of Transmittal of International Preliminary Report on Patentability for International Application No. PCT/US2006/018778 (dated Feb. 21, 2007).
Notification of Transmittal of the International Search Report and the Written Opinion of the International Searching Authority, or the Declaration for International Application No. PCT/US2006/018778 (dated May 5, 2009).
Notification of Transmittal of the International Search Report and the Written Opinion of the International Searching Authority, or the Declaration corresponding to International Application No. PCT/US2008/008945 (dated Feb. 20, 2009).
Notification of Transmittal of the International Search Report and the Written Opinion of the International Searching Authority, or the Declaration corresponding to International Application No. PCT/US2011/066843 dated Aug. 22, 2012.
Oduah et al., "Heparin: Past, present, and future." Pharmaceuticals (Basel), vol. 9, Article No. 38 (2016).
Office Action (Restriction Requirement) corresponding to U.S. Appl. No. 16/625,342 dated Dec. 16, 2021.
Office Action corresponding to U.S. Appl. No. 16/625,342 dated Nov. 4, 2022.
Office Action (Restriction Requirement) corresponding to U.S. Appl. No. 16/761,159 dated Jun. 10, 2022.
Office Action (Restriction Requirement) corresponding to U.S. Appl. No. 16/492,858 dated Jun. 30, 2021.
Office Action corresponding to Chinese Patent Application No. 201880020095.X dated Jun. 8, 2022.
Office Action corresponding to Chinese Patent Application No. 201480044429.9 dated Aug. 30, 2018.
Office Action corresponding to Chinese Patent Application No. 201480044429.9 dated Apr. 9, 2019.
Office Action corresponding to Chinese Patent Application No. 201480044429.9 dated Mar. 3, 2020.
Office Action corresponding to Chinese Patent Application No. 201880020095.X dated Sep. 22, 2021.
Office Action corresponding to European Patent Application No. 11849994.6 dated May 24, 2018.
Office Action corresponding to European Patent Application No. 11849994.6 dated Jan. 22, 2020.
Office Action corresponding to European Patent Application No. 14812890.3 dated Jun. 23, 2020.
Office Action corresponding to Japanese Patent Application No. 2016-521505 dated Jul. 30, 2019.
Office Action corresponding to Japanese Patent Application No. 2016-521505 dated Jul. 1, 2019.
Office Action corresponding to Japanese Patent Application No. 2019-549419 dated Mar. 1, 2022.
Office Action corresponding to U.S. Appl. No. 12/178,434 dated Oct. 28, 2011.
Office Action corresponding to U.S. Appl. No. 12/178,434 dated Apr. 19, 2011.
Office Action corresponding to U.S. Appl. No. 12/178,434 dated Jan. 26, 2011.
Office Action corresponding to U.S. Appl. No. 16/492,858 dated Jan. 13, 2022.
Office Action corresponding to U.S. Appl. No. 16/625,342 dated Mar. 21, 2022.
Office Action corresponding to U.S. Appl. No. 13/996,930 dated Oct. 8, 2015.
Office Action corresponding to U.S. Appl. No. 13/996,930 dated May 26, 2016.
Office Action corresponding to U.S. Appl. No. 13/996,930 dated Dec. 21, 2017.
Office Action corresponding to U.S. Appl. No. 13/996,930 dated Jul. 30, 2018.
Office Action corresponding to U.S. Appl. No. 13/996,930 dated Nov. 22, 2019.
Official Action corresponding to U.S. Appl. No. 11/920,319 dated Apr. 28, 2010.
Official Action corresponding to U.S. Appl. No. 14/898,865 dated Mar. 23, 2017.
Oliveira et al., "Neutrophils: a cornerstone of liver ischemia and reperfusion injury." Lab. Invest., vol. 98, pp. 51-62 (2018).
Ong et al., "Expression Cloning of a Human Sulfotransferase that Directs the Synthesis of the HNK-1 Glycan on the Neural Cell Adhesion Molecule and Glycolipids," The Journal of Biological Chemistry, vol. 273, No. 9, pp. 5190-5195 (Feb. 27, 1998).
Onufriev, A; Bashford, D.; Case, D. A Proteins 2004, 55, 383.
Ornitz et al., "Receptor Specificity of the Fibroblast Growth Factor Family," J. Biol. Chem., vol. 271, No. 25, pp. 15292-15297 (1996).
Ouyang et al., "Molecular Cloning and Expression of Human and Mouse Tyrosylprotein Sulfotransferase-2 and a Tyrosylprotein

(56) References Cited

OTHER PUBLICATIONS

Sulfotransferase Homologue in Caenorhabditis elegans," The Journal of Biological Chemistry, vol. 273, No. 38. pp. 24770-24774 (Sep. 18, 1998).
Ozawa et al., "Nucleotide sequence of a full-length cDNA (PST-1) for aryl sulfotransferase from rat liver," Nucleic Acids Res., vol. 18, No. 13, p. 4001 (1990).
Park et al., "Cell surface heparan sulfate proteoglycans: selective regulators of ligand-receptor encounters." J. Biol. Chem. vol. 275, pp. 29923-29926 (2000).
Patel, V. N.; Lombaert, I. M.A.; Cowherd, S. N.; Shworak, N.: Xu, Y.; Liu, J.; Hoffman, M. P. Developmental Cell 2014, 29, 662.
Pempe, et al., "Probing Structural Selectivity of Synthetic Heparin Binding to Stabilin Protein Receptors," Journal of Biol. Chem., vol. 287, No. 25, pp. 20774-20783 (Jun. 15, 2012).
Petitou et al., "A Synthetic Antithrombin III Binding Pentasaccharide is Now a Drug! What Comes Next?" Angew. Chem. Int. Ed., vol. 43, pp. 3118-3133 (2004).
Petitou et al., "Synthesis of thrombin-inhibiting heparin mimetics without side effects." Nature, vol. 398, pp. 417-422 (Apr. 1, 1999).
Pettersen, E. F.; Goddard, T. D.; Huang, C. C.; Couch, G. S.; Greenblatt, D. M.; Meng, E. C.; Ferrin, T. E. J. Comp. Chem. 2004, 25, 1605.
Pierce et al., "Inflammatory response to trauma: implications for coagulation and resuscitation." Curr. Opin. Anesthesio., vol. 27, pp. 246-252 (2014).
Pinhal et al., "Enzyme interactions in heparan sulfate biosynthesis: Uronosyl 5-epimerase and 2-O-sulfotransferase interact in vivo.," Proc. Natl. Acad. Sci. U. S. A., vol. 98, No. 23, pp. 12984-12989 (Nov. 6, 2001).
Proudfoot et al., "Glycosaminoglycan binding and oligomerization are essential for the in vivo activity of certain chemokines." Proc. Natl. Acad. Sci. USA vol. 100, pp. 1885-1890 (2003).
Pulsipher et al., "Directing Neuronal Signaling through Cell-Surface Glycan Engineering." J. Am. Chem. Soc., vol. 136, pp. 6794-6797 (2014).
Pye et al., "Heparan Sulfate Oligosaccharides Require 6-O-Sulfation for Promotion of Basic Fibroblast Growth Factor Mitogenic Activity," J. Biol. Chem., vol. 273, No. 36, pp. 22936-22942 (Sep. 4, 1998).
Raman, R.; Venkataraman, G.; Ernst, S.; Sasisekharan, R. Proc. Natl. Acad. Sci. 2003, 100, 2357.
Razi et al., "Structural and functional properties of heparin analogues obtained by chemical sulphation of *Escherichia coli* K5 capsular polysaccharide," Biochem. J., vol. 389, pp. 465-472 ,(1995).
Reizes et al., "Transgenic Expression of Syndecan-1 Uncovers a Physiological Control of Feeding Behavior by Syndecan-3," Cell, vol. 106, pp. 105-116 (Jul. 13, 2001).
Rohrmann et al., "Two N-acetylgalactosaminyltransferase are involved in the biosynthesis of chondroitin sulfate," European Journal of Biochemistry, vol. 148, pp. 463-469 (1985).
Roman-Blas et al., "The combined therapy with chondroitin sulfate plus glucosamine sulfate or chondroitin sulfate plus glucosamine hydrochloride does not improve joint damage in an experimental model of knee osteoarthritis in rabbits." Eur. J. Pharmacol., vol. 794, pp. 8-14 (2017).
Rosenberg et al., "Heparan Sulfate Proteoglycans of the Cardiovascular System Specific Structures Emerge But How Is Synthesis Regulated?" J. Clin. Invest., vol. 99, No. 9, pp. 2062-2070 (May 1997).
Saeki et al., "Molecular Cloning, Expression, and Characterization of a Novel Mouse Liver SULT1B1 Sulfotransferase," J. Biochem., vol. 124, pp. 55-64 (1998).
Sala et al., "UDP-N-trifluoroacetylglucosamine as an alternative substrate in N-acetylglucosaminyltransferase reactions", Carbohydrate Research, vol. 306, pp. 127-136 (1998).
Saribas et al., "Production of N-sulfated 1-38 polysaccharides using yeast-expressed N-deacetylase/N-sulfotransferase-1 (NDST-I)," Glycobiology, vol. 14, pp. 1217-1228 (2004).
Sarris et al., "Inflammatory chemokines direct and restrict leukocyte migration within live tissues as glycan-bound gradients." Curr. Biol. vol. 22, pp. 2375-2382 (2012).
Sasisekharan et al., "Roles of Heparan-Sulphate Glycosaminoglycans in Cancer," Nat. Rev. Cancer, vol. 2, pp. 521-528 (Jul. 2002).
Sattelle, B. M.; Almond, A. Glycobiology 2011, 21, 1651.
Sattelle, B. M.; Hansen, S. U.; Gardiner, J. M.; Almond, A. J Am Chem Soc 2010, 132, 13132.
Schroeder et al., "Protamine neutralization of low molecular weight heparins and their oligosaccharide components," Anal Bioanal Chem, vol. 399, pp. 763-771 (2011).
Schwartz et al., "Virogenic BrdU and BrdU-sensitive DNA sequences are disproportionately concentrated in the template-active chromatin of rat embryo cells," Nuc Acids Res., vol. 6, No. 2, pp. 745-755 (Feb. 1979).
Schworer, R.; Zubkova, 0. V.; Turnbull, J. E.; Tyler, P. C. Chem. Eur. J. 2013, 19, 6817.
Sheng et al., "Influenced of Phenylalanines 77 and 138 on the Stereospecifity of Aryl Sulfotransferase IV," Drug Metabol. Dispos., vol. 32, No. 5, pp. 559-565 (2004).
Sheng et al., "The Dominating Role of N-Deacetylase/N-Sulfotransferase 1 in Forming Domain Structures in Heparan Sulfate," The Journal of Biological Chemistry, vol. 286, No. 22, pp. 19768-19776 (Jun. 3, 2011).
Shiori et al., "Sequence determination of synthesized chondroitin sulfate dodecasaccharides." Glycobiology, vol. 26, pp. 592-606 (2016).
Shively et al., "Formation of Anhydrosugars in the Chemical Depolymerization of Heparin," Biochemistry, vol. 15, No. 18, pp. 3932-3942 (1976).
Shriver et al., "Glycomics: A Pathway to a Class of New and Improved Therapeutics," Nat. Rev. Drug Discov., vol. 3, pp. 863-873 (Oct. 2004).
Shukla et al., "A Novel Role for 3-O-Sulfated Heparan Sulfate in Herpes Simplex Virus 1 Entry," Cell, vol. 99, pp. 13-22 (Oct. 1, 1999).
Shukla et al., "Herpes viruses and heparan sulfate: an intimate relationship in aid of viral entry," The Journal of Clinical Investigation, vol. 108, No. 4, pp. 503-510 (Aug. 2001).
Shworak et al., "Molecular Cloning and Expression of Mouse and Human cDNAs Encoding Heparan Sulfate D-Glucosaminyl 3-O-Sulfotransferase," The Journal of Biological Chemistry, vol. 272, No. 44, pp. 28008-28019 (1997).
Singh, A; Tessier, M. B.; Pederson, K.; Wang, X.; Venot, A P.; Boons, G.-J.; Prestegard, J. H.; Woods, R. J. Can. J. Chem. 2016, 10.1139/cjc.
Sismey-Ragatz, et al., "Chemoenzymatic Synthesis with Distinc Pasteurella Heparosan Synthases," J. Biol. Chem., vol. 282, No. 39, pp. 28321-28327 (Jul. 11, 2007).
Smeds et al., "Substrate specificities of mouse heparan sulphate glucosaminyl 6-O-sulphotransferases," Biochem. J, vol. 372, pp. 371-380 (2003).
Smith et al., "Comparison of Biosequences," Adv. Appl. Math, vol. 2, pp. 482-489 (1981).
Solera et al., "Chondroitin sulfate tetrasaccharides: synthesis, three-dimensional structure and interaction with midkine." Chemistry, vol. 22, pp. 2356-2369 (2016).
Stabler et al., "Chondroitin sulphate inhibits NF-κB activity induced by interaction of pathogenic and damage associated molecules." Osteoarthritis and Cartilage, vol. 25, pp. 166-174 (2017).
STN record for Chen et al., dissertation, "Towards de novo synthesis of structure-defined oligosaccharides with heparan sulfate u biosynthetic enzymes", entered into STN: Apr. 20, 2009. 1 page.
Sugiura et al., "Molecular dissection of placental malaria protein VAR2CSA interaction with a chemo-enzymatically synthesized chondroitin sulfate library." Glycoconj. J., vol. 33, pp. 985-994 (2016).
Sugiura et al., "Sequential synthesis of chondroitin oligosaccharides by immobilized chondroitin polymerase mutants." Glycoconj. J., vol. 25, pp. 521-530 (2008).
Sugiura et al., "Baculovirus Envelope Protein ODV-E66 is a Novel Chondroitinase with Distinct Substrate Specificity." J. Biol. Chem.; vol. 286; pp. 29026-29034 (2011).

(56) References Cited

OTHER PUBLICATIONS

Sugiura et al., "Construction of a Chondroitin Sulfate Library with Defined Structures and Analysis of Molecular Interactions." J. Biol. Chem., vol. 287, pp. 43390-43400 (2012).
Sundaram, M. et al., "Rational design of low-molecular weight heparins with improved in vivo activity," Proc. Natl. Acad. Sci., vol. 100, No. 2, pp. 651-656 (Jan. 21, 2003).
Supplemental Notice of Allowability and Interview Summary corresponding to U.S. Appl. No. 14/898,865 dated Jan. 12, 2018.
Szajek et al., "The US regulatory and pharmacopeia responses to the global heparin contamination crisis." Nat. Biotechnol. vol. 34, pp. 625-630 (2016).
Takagaki et al., "Enzymatic Reconstruction of a Hybrid Glycosaminoglycan Containing 6-Sulfated, 4-Sulfated, and Unsulfated N-Acetylgalactosamine" Biochemical and Biophysical Research Communications vol. 258 pp. 741-744 (Year: 1999).
Tamura et al., "Synthesis of chondroitin sulfate E octasaccharide in a repeating region involving an acetamide auxiliary." Carbohydr. Res., vol. 343, pp. 39-47 (2008).
Tecle, E.; Diaz-Balzac, C. A.; Bulow, H. E. G3 (Bethesda) 2013, 3, 541.
Teng et al., "Molecular functions of syndecan-1 in disease." Matrix Biol., vol. 31, pp. 3-16 (2012).
Thacker, B. E.; Seamen, E.; Lawrence, R.; Parker, M. W.; Xu, Y.; Liu, J.; Vander, K. C. W.; Eska, J. D. ACS Chem. Biol. 2016, 11, 971.
Thompson et al., "CLUSTAL W: improving the sensitivity of progressive multiple sequence alignment through sequence weighting, position-specific gap penalties and weight matrix choice," Nucleic Acids Res., vol. 22, No. 22, pp. 4673-4680 (1994).
Tohu et al., Anti-Xa and Anti-IIa Drugs Alter International Normalized Ratio Measurements: Potential Problems in the Monitoring of Oral Anticoagulants Clin. Appl. Thrombos Hemostas, vol. 10, pp. 301-309 (2004).
Tsau, C.; Ito, M.; Gromova, A.: Hoffman, M. P.; Meech, R.; Makarenkova, H. P. Development 2011, 138, 3307.
Tsung et al., "HMGB1 release induced by liver ischemia involves Toll-like receptor 4-dependent reactive oxygen species production and calcium-mediated signaling." J. Exp. Med., vol. 204, pp. 2913-2923 (2007).
Tsung et al., "The nuclear factor HMGB1 mediates hepatic injury after murine liver ischemia-reperfusion." J. Exp. Med., vol. 201, pp. 1135-1143 (2005).
Uchimura et al., "Molecular Cloning and Characterization of an N-Acetylglucosamine-6-O-sulfotransferase," The Journal of Biological Chemistry, vol. 273, No. 35, pp. 22577-22583 (Aug. 28, 1998).
Vann et al., "The Structure of the Capsular Polysaccharide (K5 Antigen) of Urinary-Tract-Infective *Escherichia coli* 010 : K5 : H4 A Polymer Similar to Desulfo-Heparin," Eur. J. Biochem, vol. 116, pp. 359-364 (1981).
Venereau et al., "HMGB1 as biomarker and drug target." Pharmacol. Res. vol. 111, pp. 534-544 (2016).
Wang et al., "*E. coli* K5 fermentation and the Preparation of Heparosan, a Bioengineered Heparin Precursor," Biotechnol. Bioeng, vol. 107, No. 7, pp. 968-977 (Dec. 15, 2010).
Wang et al., "Edothelial heparan sulfate deficiency impairs L-selectin- and chemokine-mediated neutrophil trafficking during inflammatory responses." Nat. Immunol. vol. 6, pp. 902-910 (2005).
Weber et al., "Renal dysfunction in liver transplant recipients: Evaluation of the critical issues." Liver Transplant., vol. 18, pp. 1290-1301 (2012).
Weitz et al., "Beyond heparin and warfarin: the new generation of anticoagulants," Expert Opin. Investig. Drugs, vol. 16, No. 3, pp. 271-282 (2007).
Weitz, "Potential of new anticoagulants in patients with cancer," Thromb. Res., vol. 125 (Suppl 2), pp. S30-S35 (2010).
Wildhagen et al., "Nonanticoagulant heparin prevents histone-mediated cytotoxicity in vitro and improves survival in sepsis." Blood vol. 123, pp. 1098-1101 (2014).
Willis et al., "Examination of the Kinetics of Herpes Simplex Virus Glycoprotein D Binding to the Herpesvirus Entry Mediator, Using Surface Plasmon Resonance," J. Virol., vol. 72, pp. 5938-5947 (Jul. 1998).
Wishart et al., "A single mutation converts a novel phosphotyosine binding domain into a dual-specificity phosphatase," J. Biol. Chem., vol. 270, No. 45, pp. 26782-26785 (1995).
Witkowski et al., "Conversion of b-ketoacyl synthase to a Malonyl Decarboxylase by replacement of the active cysteine with glutamine," Biochemistry, vol. 38, pp. 11643-11650 (1999).
Written Opinion corresponding to International Application No. PCT/US2019/037993 dated Oct. 18, 2019.
Written Opinion of the International Searching Authority Corresponding to International Application No. PCT/US 2018/021986 dated Aug. 1, 2018.
WuDunn et al., "Initial interaction of herpes simplex virus with cells is binding to heparan sulfate," J. Virol., vol. 63, No. 1, pp. 52-58 (1989).
Xia et al., "Heparan Sulfate 3-O-Sulfotransferase Isoform 5 Generates Both an Antithrombin-binding Site and an Entry Receptor for Herpes Simplex Virus, Type 1," J. Biol. Chem., vol. 277, No. 40, pp. 37912-37919 (2002).
Xu et al., "Characterization of heparan sulphate 3-O-sulphotransferase isoform 6 and its role in assisting the entry of herpes simplex virus type 1" Biochem. J., vol. 385, pp. 451-459 (2005).
Xu et al., Chemoenzymatic Synthesis of Homogeneous Ultralow Molecular Weight Heparins, Science, vol. 334, pp. 498-501 (Oct. 2011).
Xu et al., "Heparan sulfate is essential for high mobility group protein 1 (HMGB1) signaling by the receptor for advanced glycation end products (RAGE)." J. Biol. Chem. vol. 286, pp. 41736-41744 (2011).
Xu et al., "Homogeneous low-molecular-weight heparins with reversible anticoagulant activity." Nat. Chem. Biol. vol. 10, pp. 248-250 (2014).
Xu et al., Synthetic oligosaccharides can replace animal-sourced low-molecular weight heparins Sci. Transl. Med. vol. 9, eaan5954 (2017).
Xu J, Zhang X, Monestier M, Esmon NL, and Esmon CT. Extracellular histones are mediators of death through TLR2 and TLR4 in mouse fatal liver injury. J Immunol. 2011;187:2626-31.
Xu J, Zhang X, Pelayo R, Monestier M, Ammollo CT, Semeraro F, et al. Extracellular histones are major mediators of death in sepsis. Nat Med. 2009;15:1318-21.
Xu, D. et al., "Engineering sulfotransferases to modify heparan sulfate," Nat Chem Biol, vol. 4, No. 3, pp. 200-202 (Mar. 2008).
Xu, D.; Esko, "Demystifying Heparan Sulfate-Protein Interactions," J. Annu Rev Biochem. 2014, 83, 129.
Xu, D.; Olson, J.; Cole, J. N.; van Wijk, X. M.; Brinkmann, V.; Zychlinsky, A.; Nizet, V.; Eska, J. D.; Chang, Y. C. Infect. Immun. 2015, 83, 3648.
Xue et al., "Impact of donor binding on polymerization catalyzed by KfoC by regulating the affinity of enzyme for acceptor." Biochim. Biophys. Acta, vol. 1860, pp. 844-855 (2016).
Yang et al. Effects of 3' -phosphoadenosine 5'-phosphate on the activity and folding of phenol sulfotransferase. Chem.-Biol. Interact. 109: 129-135 (1998).
Yang et al., "An Approach to Synthesize Chondroitin Sulfate-E (CS-E) Oligosaccharide Precursors." J. Organic Chem., vol. 83, pp. 5897-5908 (2018).
Yang et al., "Middle region of the Borrelia burgdorferi surface-located protein 1 (Lmp1) interacts with host chondroitin-6-sulfate and independently facilitates infection." Cell Microbiology, vol. 18, 97-110 (2016).
Yang et al., "Two Phenol Sulfotransferase Species from One cDNA: Nature of the Differences," Protein Expression Purif, vol. 8, pp. 423-429 (1996).
Yang, J.; Hsieh, P.; Liu, X.; Zhou, W.; Zhang, X.; Zhao, J.; Xu, Y.; Zhang, F.; Linhardt, R. J.; Liu, J. Chem Comm 2017, 53, 1743.
Yang, Z.; Lasker, K.; Schneidman-Duhovny, D.; Webb, B.; Huang, C. C.; Pettersen, E. F.; Goddard, T. D.; Meng, E. C.; Sali, A; Ferrin, T. E. J. Struct. Biol. 2012, 179, 269.

(56) References Cited

OTHER PUBLICATIONS

Yoshinari et al., "Molecular Cloning, Expression, and Enzymatic Characterization of Rabbit Hydroxysteroid Sulfotransferase AST-RB2 (ST2A8)," J. Biochem., vol. 123, pp. 740-746 (1998).

Yu et al., "Highly Efficient Chemoenzymatic Synthesis of Beta1-3-Linked Galactosides," Chemical Communications, vol. 46(40), pp. 7507-7509 (2010).

Yusa et al., "N-Linked Oligosaccharides on Chondroitin 6-Sulfotransferase-1 Are Required for Production of the Active Enzyme, Golgi Localization, and Sulfotransferase Activity toward Keratan Sulfate." J. Biol. Chem., vol. 281, pp. 20393-20403 (2006).

Zhang et al., "6-O-Sulfotransferase-1 Represents a Critical Enzyme in the Anticoagulant Heparan Sulfate Biosynthetic Pathway*," J. Biol. Chem., vol. 276, pp. 42311-42321 (2001).

Zhang et al., "Solution Structures of Chemoenzymatically Synthesized Heparin and Its Precursors," J. Am. Chem. Soc., vol. 130, pp. 12998-13007 (2008).

Zhang et al., "The Effect of Precursor Structures on the Action of Glucosaminyl 3-O-Sulfotransferase-1 and the Biosynthesis of Anticoagulant Heparan Sulfate," J. Biol. Chem., vol. 276, No. 31, pp. 28806-28813 (2001).

Zhao et al. "Enzymatic route to preparative-scale synthesis of UDP-GlcNAc/GalNAc, their analogues and GDP-fucose," Nat. Protoc., vol. 5, No. 4, pp. 636-646 (2010).

Zhou et al. "Expression of heparin sulfate sulfotransferases in Kluyveromyces lactis and preparation of 3'-phsphoadenosie-5'-phosphosulfate," Glycobiology, vol. 21, No. 6, pp. 771-780 (2011).

Zitvogel et al., "Decoding cell death signals in inflammation and immunity." Cell, vol. 140, pp. 798-804 (2010).

Zong, C.; Huang, R.; Condac, E.; Chiu, Y.; Xiao, W.; Li, Z. Q.; Lu, W.; Ishihara, M.; Wang, S.; Ramiah, A.; Stickney, M.; Azadi, P.; Amster, I. J.; Moremen, K. W.; Wang, L.; Sharp, J. S.; Boons, G.-J. J. Am. Chem. Soc. 2016, 138, 13059.

Beeson et al., "Inhibition of Binding of Malaria-Infected Erythrocytes by a Tetradecasaccharide Fraction from Chondroitin Sulfate A," Infection and Immunity vol. 66 No. 7 pp. 3397-3402 (Year: 1998).

Office Action (Final) corresponding to U.S. Appl. No. 16/625,342 dated Nov. 4, 2022.

* cited by examiner

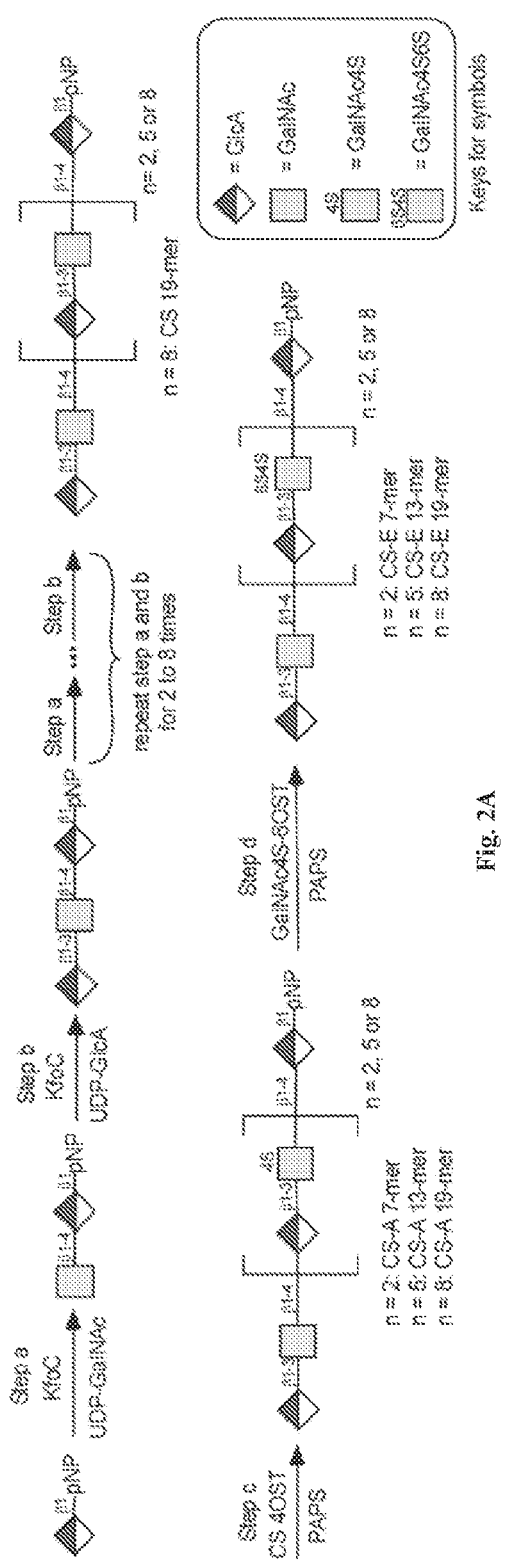
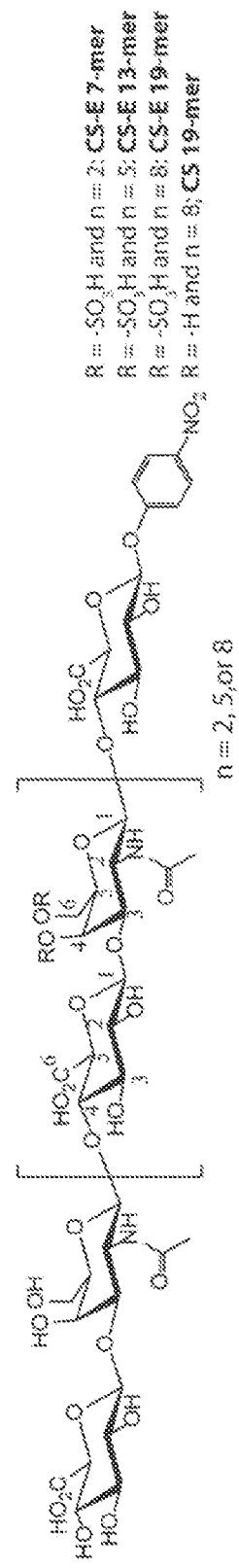
Fig. 2A
Fig. 2B

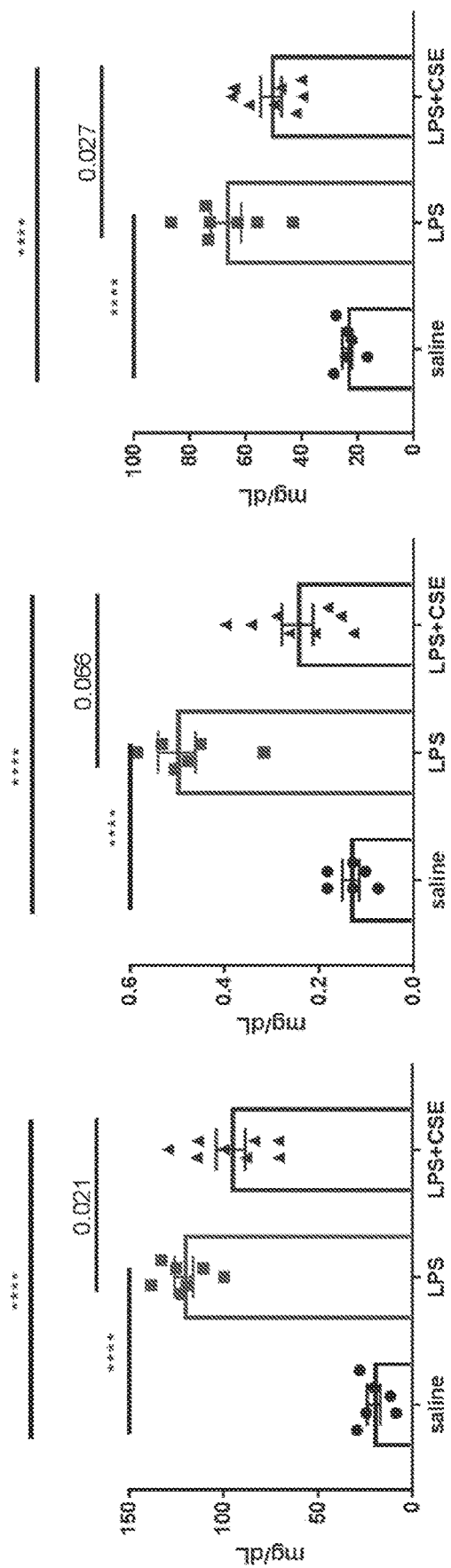

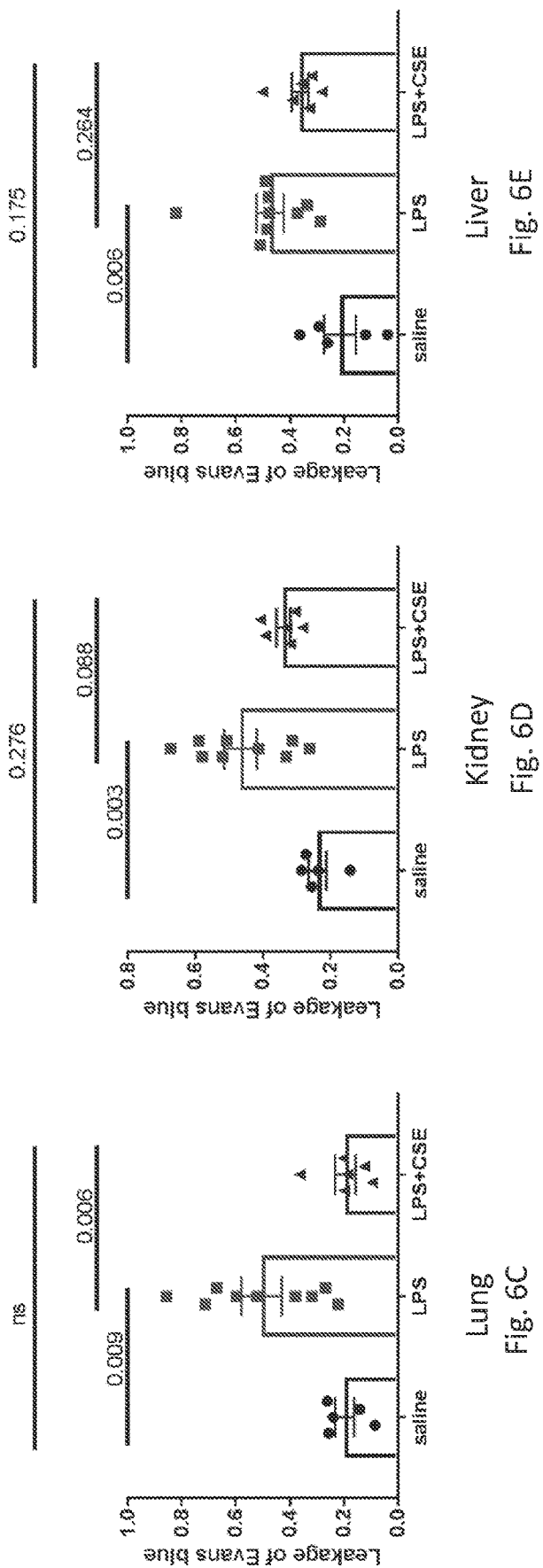

CELL PROTECTIVE METHODS AND COMPOSITIONS

CROSS-REFERENCE TO RELATED APPLICATIONS

This application is a national stage filing of PCT International Application No. PCT/US2019/037993, filed Jun. 19, 2019, incorporated herein by reference in its entirety, which claims benefit of U.S. Provisional Application Ser. No. 62/687,540, filed Jun. 20, 2018, herein incorporated by reference in its entirety.

STATEMENT OF FEDERAL SUPPORT

This invention was made with government support under Grant Numbers GM102137 & HL094463 awarded by the National Institutes of Health. The government has certain rights in the invention.

TECHNICAL FIELD

The subject matter disclosed herein relates generally to cell protective methods and compositions. More specifically, disclosed herein are chondroitin sulfate compounds, and methods of using the same to treat histone toxicity and related conditions, including sepsis.

BACKGROUND

Histones are basic proteins that are involved in the packaging of DNA to form chromatin. Histones effectively pack DNA into the cell nucleus and regulate access to the genetic information contained within the DNA.

Histones have a relatively strong positive charge, and when not bound to chromatin can cause harmful effects within a cell or in an extracellular environment. Thus, histone levels are tightly regulated intracellularly via various mechanisms. However, numerous biological conditions can induce an accumulation of non-chromatin-bound histones, also referred to as "free" or "excess" histones. Free histones in a cellular environment can cause significant cellular death, as can be seen in sepsis, trauma, ischemia/reperfusion injury and autoimmune disease. The cytotoxic effect of histones can be related to their acting as damage-associated molecular pattern proteins, activating the immune system and/or causing further cytotoxicity. The cytotoxic effects of free histones can lead to acute organ injury and mortality.

A need remains for treatments and therapeutic approaches for histone toxicity and related conditions.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

Provided in some embodiments are methods of treating histone toxicity in a subject, the methods comprising providing a subject in need of histone toxicity treatment, and administering to the subject a chondroitin sulfate compound, wherein the histone toxicity in the subject is treated. In some aspects, the subject can be suffering from sepsis. The subject can be a human subject. The chondroitin sulfate compound can comprise a CS backbone, CS-A, CS-E, CS-C and/or combinations thereof. In some aspects, the chondroitin sulfate compound comprises chondroitin sulfate backbone 19 mer, CS-A 19 mer, CS-C 19 mer, CS-E 19 mer, CS backbone 13 mer, CS-A 13 mer, CS-C 13 mer, CS-E 13 mer and/or combinations thereof. In some embodiments, the chondroitin sulfate compounds can comprise one or more of the following structures:

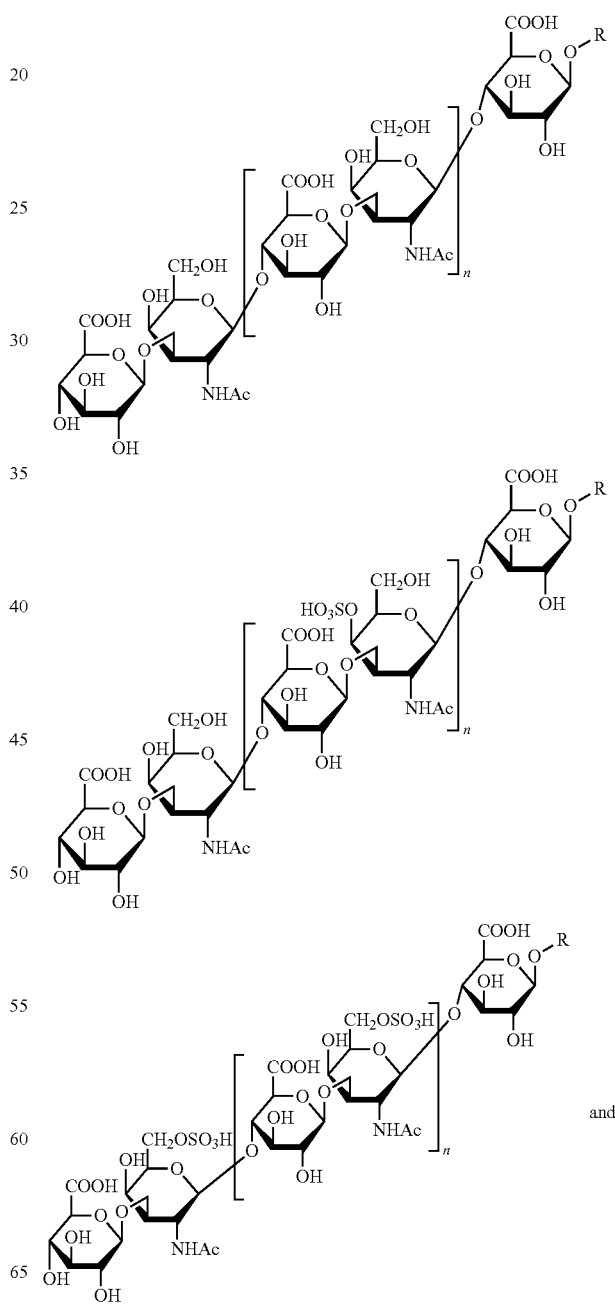

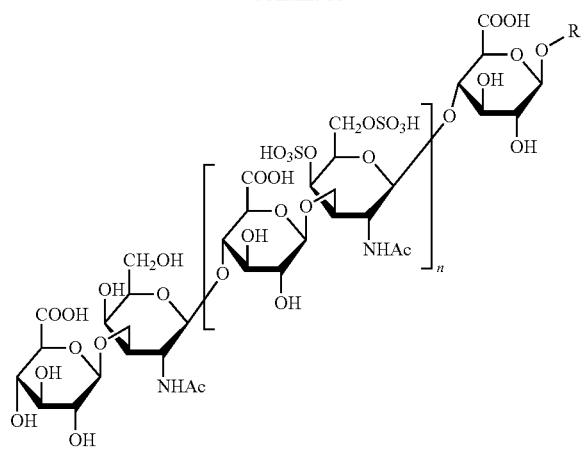

wherein R is selected from the group consisting of —H, alkyl (such as but not limited to —CH$_3$ or —CH$_2$CH$_3$), substituted alkyl, aryl, and substituted aryl (such as but not limited to a p-nitrophenyl group), wherein n is 1, 2, 3, 4, 5, 6, 7 or 8.

In some aspects, the chondroitin sulfate compounds can be administered as part of a pharmaceutical composition. The pharmaceutical compositions can comprise a CS compound and a pharmaceutically acceptable carrier or adjuvant for administration of the CS.

In some embodiments, provided herein are pharmaceutical compositions for use in treating histone toxicity and/or sepsis, the compositions comprising one or more chondroitin sulfate compounds and a pharmaceutically acceptable carrier. The chondroitin sulfate compounds can comprises a CS backbone, CS-A, CS-E, CS-C and/or combinations thereof. The chondroitin sulfate compounds can comprise chondroitin sulfate backbone 19 mer, CS-A 19 mer, CS-C 19 mer, CS-E 19 mer, CS backbone 13 mer, CS-A 13 mer, CS-C 13 mer, CS-E 13 mer and/or combinations thereof. The chondroitin sulfate compounds can comprise one or more of the following structures:

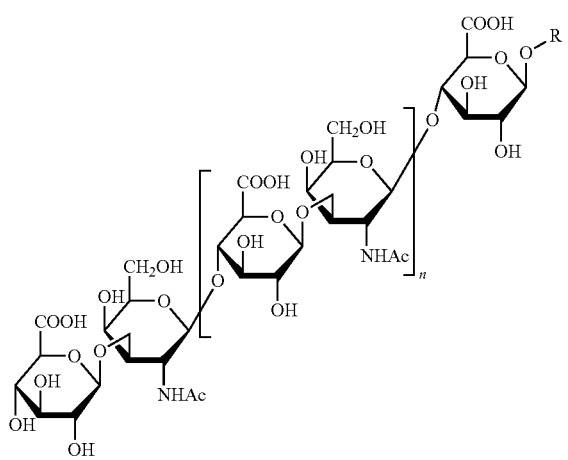

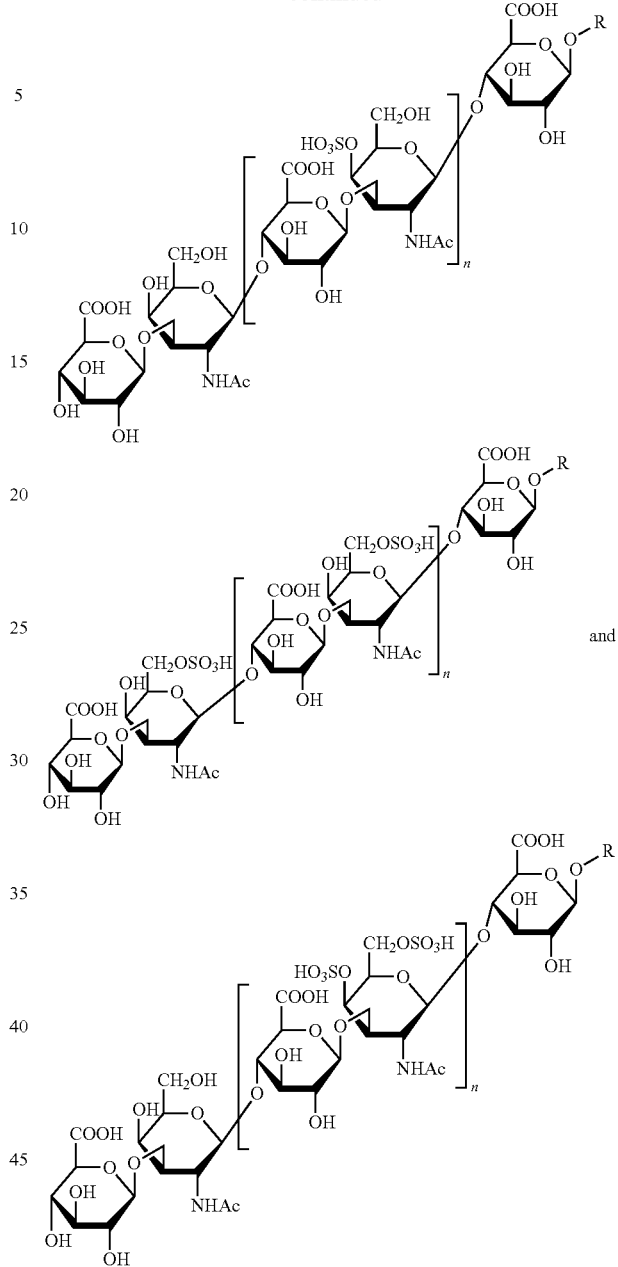

wherein R is selected from the group consisting of —H, alkyl (such as but not limited to —CH$_3$ or —CH$_2$CH$_3$), substituted alkyl, aryl, and substituted aryl (such as but not limited to a p-nitrophenyl group), wherein n is 1, 2, 3, 4, 5, 6, 7 or 8.

Also provided herein are methods of treating sepsis in a subject, the methods comprising providing a subject in need of sepsis treatment, and administering to the subject a chondroitin sulfate compound, wherein the sepsis in the subject is treated. The subject can be a human subject. The chondroitin sulfate compounds can comprise a CS backbone, CS-A, CS-E, CS-C and/or combinations thereof. In some aspects, the chondroitin sulfate compounds can comprises chondroitin sulfate backbone 19 mer, CS-A 19 mer, CS-C 19 mer, CS-E 19 mer, CS backbone 13 mer, CS-A 13 mer, CS-C 13 mer, CS-E 13 mer and/or combinations thereof. In some aspects, within these methods of treating sepsis the chondroitin sulfate compounds can comprise one or more of the following structures:

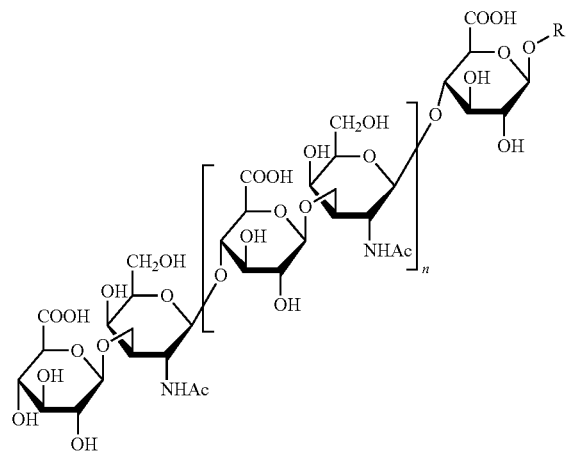

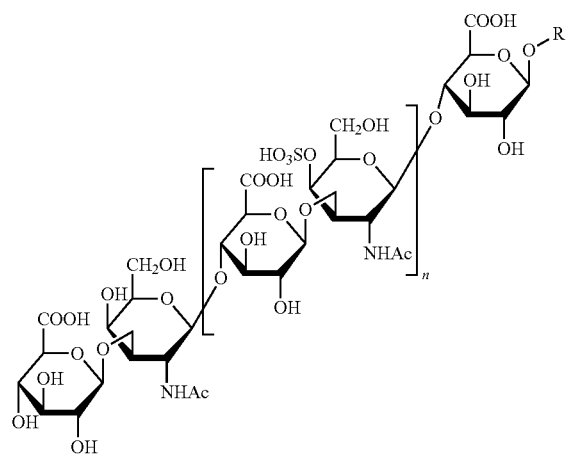

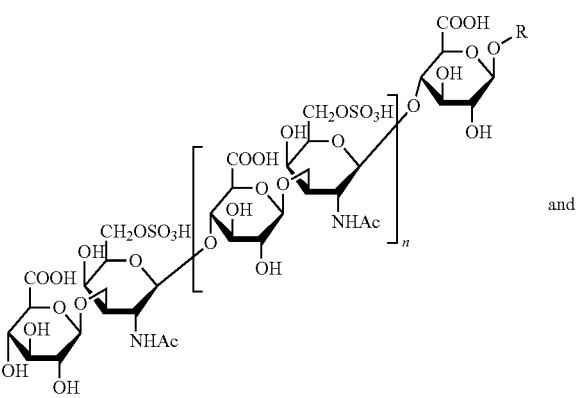

-continued

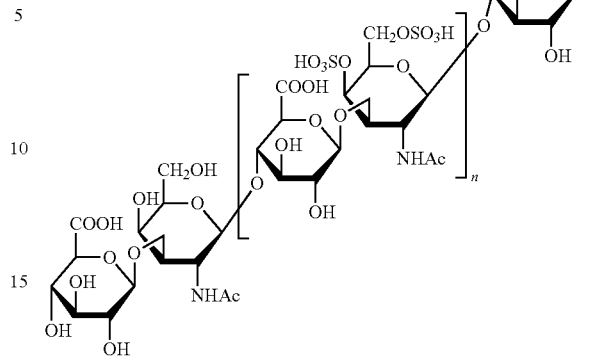

wherein R is selected from the group consisting of —H, alkyl (such as but not limited to —CH$_3$ or —CH$_2$CH$_3$), substituted alkyl, aryl, and substituted aryl (such as but not limited to a p-nitrophenyl group), wherein n is 1, 2, 3, 4, 5, 6, 7 or 8. In some aspects, the chondroitin sulfate compounds can be administered as part of a pharmaceutical composition. The pharmaceutical compositions can comprise a CS compound and a pharmaceutically acceptable carrier or adjuvant for administration of the CS.

These and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, drawings and examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, can be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

Like numbers refer to like elements throughout. In the figures, the thickness of certain lines, layers, components, elements or features can be exaggerated for clarity. Where used, broken lines illustrate optional features or operations unless specified otherwise.

For a more complete understanding of the presently disclosed subject matter, reference is now made to the below drawings.

Figures 1A, 1B:
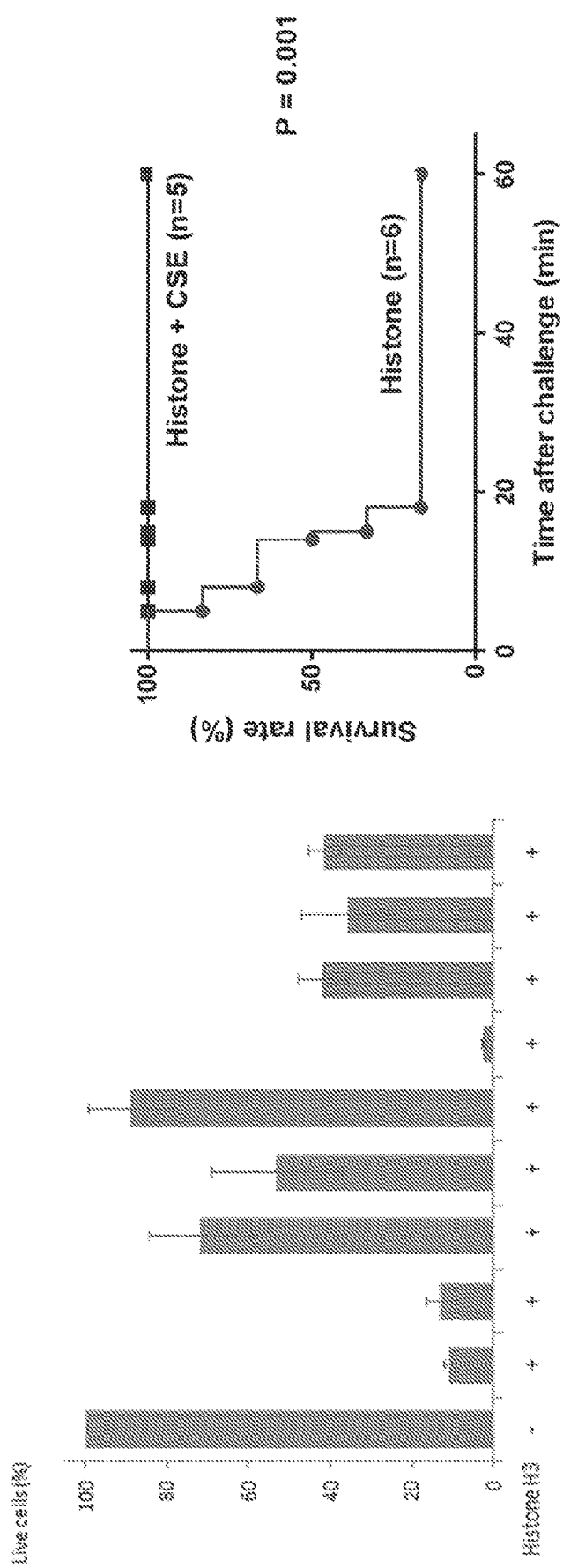

FIG. 1A is a histogram of data from studies evaluating the effectiveness of synthesized CS oligosaccharides in neutralizing histone cellular toxicity in a cell-based assay model.

FIG. 1B is a graphical depiction of data from studies evaluating the effect of synthesized CS oligosaccharides on the survival rate of mice treated by histone together with CS oligosaccharides. The survival rate of mice receiving CS oligosaccharides treatment was 100%, whereas none of the mice exposed to histones and receiving no CS therapy survived.

FIG. 2A is a schematic illustration showing enzymatic synthesis routes and methods for CS oligosaccharides as disclosed herein, including for example CS-E oligosaccharides. FIG. 2A shows the scheme to synthesize CS-E 7-mer, 13-mer and 19-mer, presented in shorthand symbols.

FIG. 2B is a schematic illustration of the chemical structures of four different CS oligosaccharides synthesized according to FIG. 2A, and described further herein.

Figure 3A:
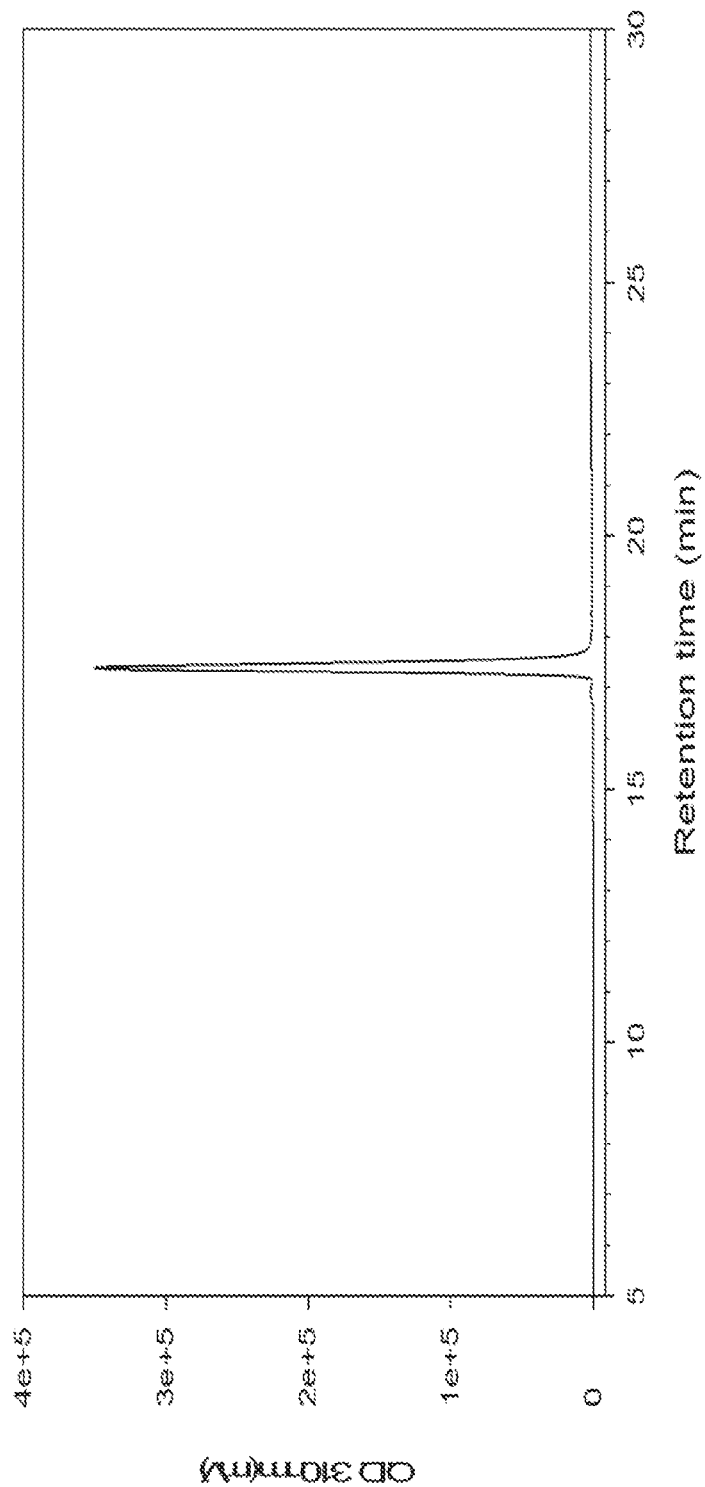
Figure 3B:
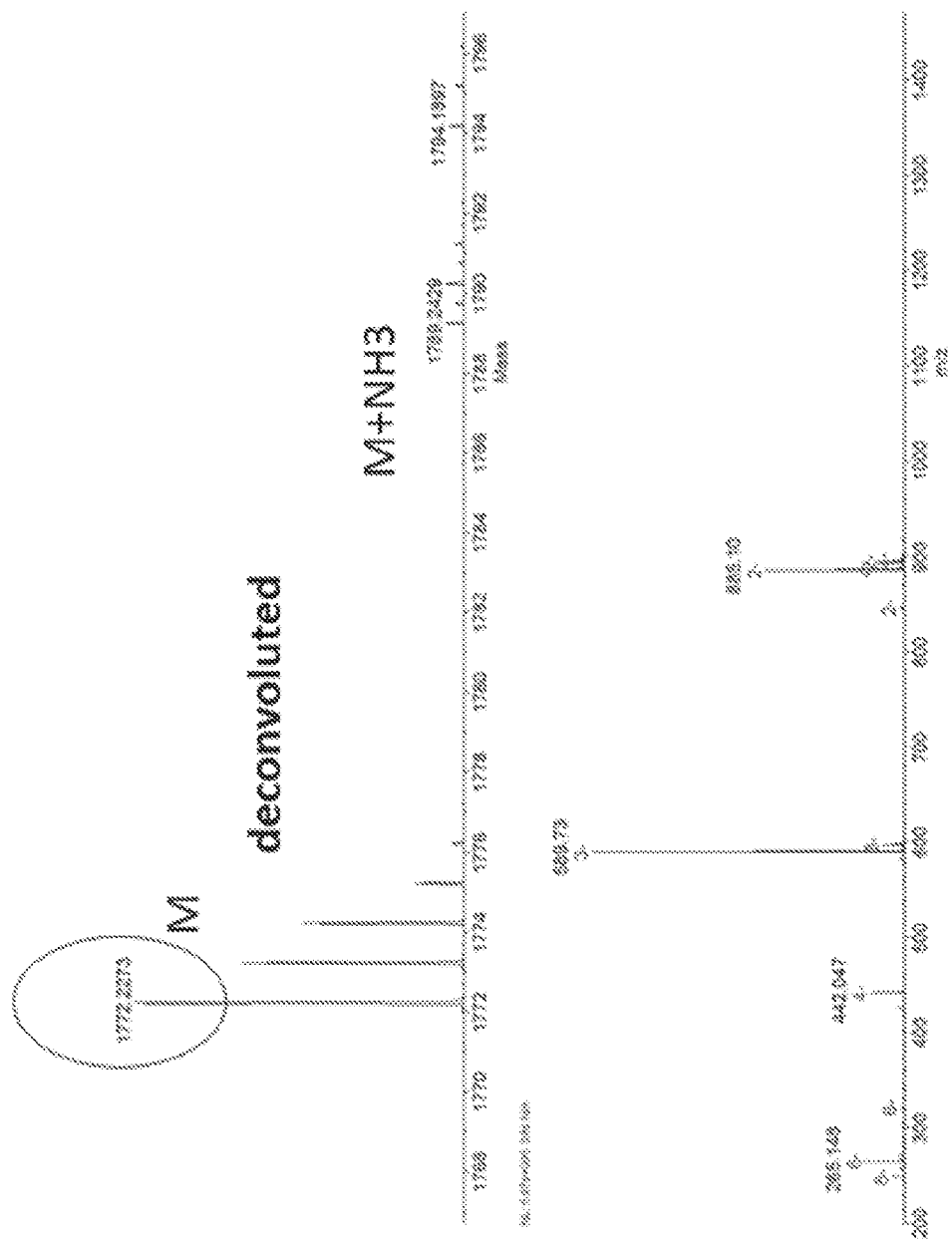

FIGS. 3A and 3B show the purity and structural analysis of CS-E 7-mer. FIG. 3A shows the DEAE-HPLC chromatogram of CS-E 7-mer, while FIG. 3B shows the high-resolution MS spectrum of CS-E 7-mer. The measure molecular mass for CS-E 7-mer is 1772.227, which is similar to the calculated molecular mass of 1772.221.

Figure 4A:
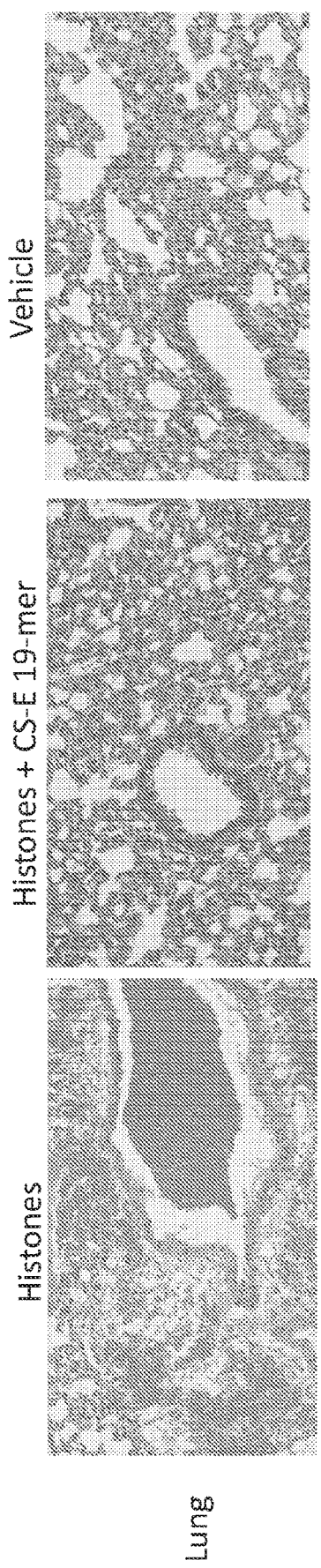

FIG. 4A shows representative images and quantitation of hematoxylin and eosin (H&E) staining of formalin fixed paraffin-embedded lung tissues from mice intoxicated with histone (75 mg/kg) with or without CS-E 19-mer (50 mg/kg) treatment.

Figure 4B:
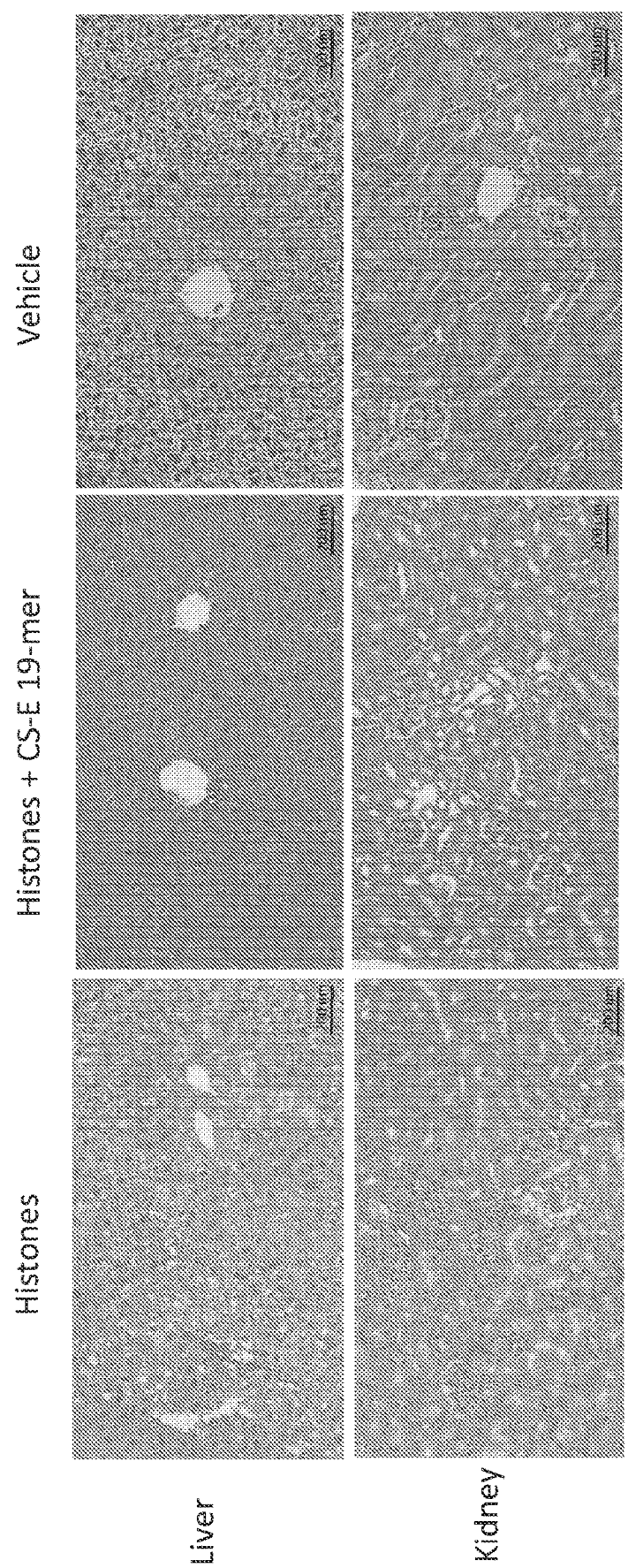

FIG. 4B shows representative images of hematoxylin and eosin (H&E) staining of formalin fixed paraffin-embedded kidney and liver tissues from mice intoxicated with histone (75 mg/kg) with or without CS-E 19-mer (50 mg/kg) treatment.

Figure 5A:
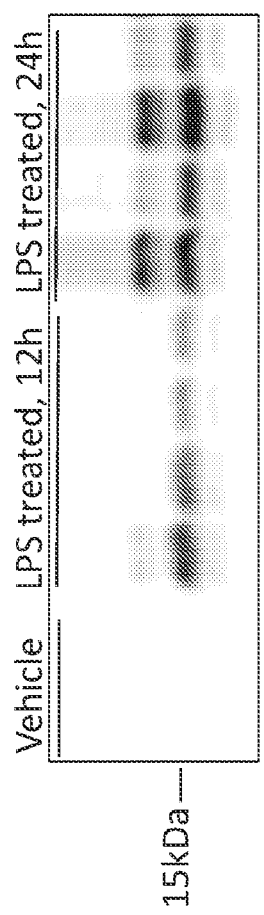
Figure 5B:
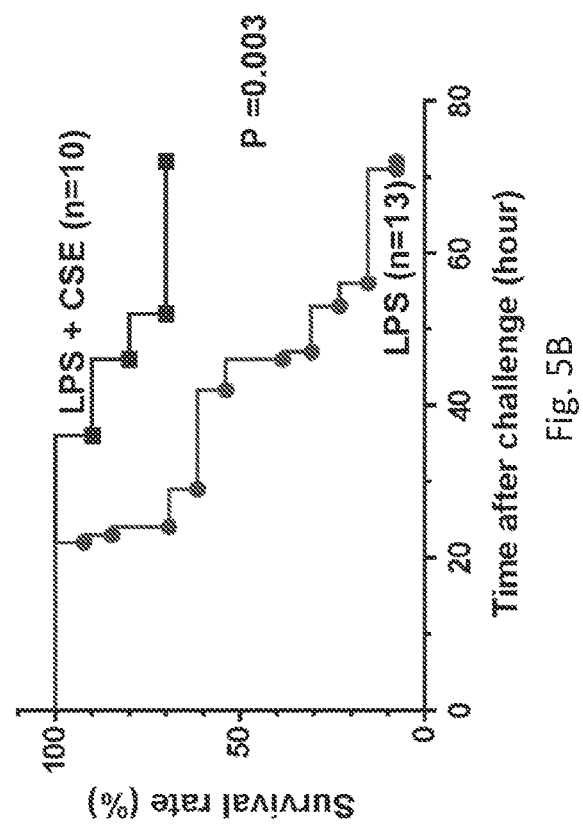

FIGS. 5A through 5E show data illustrating that CS-E 19-mer protects against death and organ damages caused by bacterial lipopolysaccharides (LPS). FIG. 5A is an image of a Western blot for the analysis of histone H3 in mice plasma after the administration of bacterial lipopolysaccharide (6 mg/kg). FIG. 5B is a graphical depiction of survival plots of mice administered with LPS (6 mg/kg) with or without the treatment of CS-E 19-mer (0.5 mg/kg). Ten animals were in LPS/CS-E 19-mer cohort, and thirteen animals were included in LPS treated cohort. Kaplan-Meier survival curves by log-rank test using GraphPad Prism software was performed to obtained. P=0.003. FIGS. 5C through 5E shows the plasma concentrations of different biomarkers, including BUN, creatinine and AST, respectively, in animals treated with phosphate-buffered saline, LPS and LPS/CS-E 19-mer.

Figure 6A:
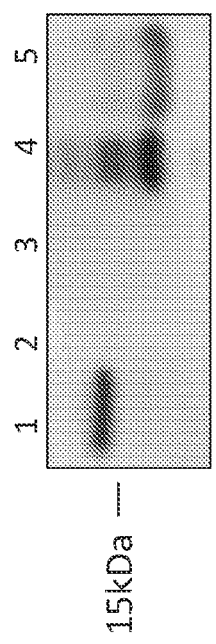
Figure 6B:
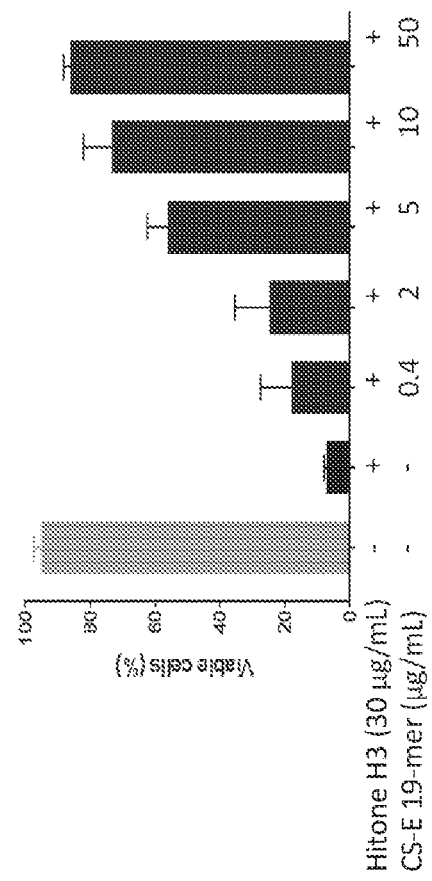

FIGS. 6A through 6E show data illustrating that CS-E 19-mer forms a complex with histone to protect against histone-induced endothelial cell damage. FIG. 6A is an image of a Western blot analysis of mouse plasma samples with or without avidin-agarose affinity column purification. Lane 1 is histone H3. Lane 2 is untreated mouse plasma. Lane 3 is untreated mouse plasma incubated with biotinylated CS-E 19-mer after affinity purification. Lane 4 is LPS-treated mouse plasma. Lane 5 is LPS-treated mouse plasma with biotinylated CS-E 19-mer after affinity purification. FIG. 6B is a graph of data showing cytotoxicity of histone toward endothelial with or without CS oligosaccharides. Cell damage, as measured by flow cytometry for propidium iodide (PI) staining, in EA.hy926 cells cultures with histone H3 (30 µg/mL) without or with different concentrations of CS oligosaccharides. FIGS. 6C through 6E shows the concentrations of leaked Evans blue from the lung, kidney and liver, respectively, under the treatment of saline, LPS or LPS/CS-E 19-mer.

DETAILED DESCRIPTION

The presently disclosed subject matter now will be described more fully hereinafter, in which some, but not all embodiments of the presently disclosed subject matter are described. Indeed, the disclosed subject matter can be embodied in many different forms and should not be construed as limited to the embodiments set forth herein; rather, these embodiments are provided so that this disclosure will satisfy applicable legal requirements.

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the present disclosure and the claims.

All publications, patent applications, patents and other references cited herein are incorporated by reference in their entireties for the teachings relevant to the sentence and/or paragraph in which the reference is presented.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of" and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein, the term "substantially," when referring to a value, an activity, or to an amount of a composition, mass, weight, temperature, time, volume, concentration, percentage, etc., is meant to encompass variations of in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed apparatuses and devices. For example, a composition is "substantially pure" when it is at least 60% pure, or at least 75%, or at least 80%, or at least 85%, or at least 90%, or at least 95% pure, and, in certain cases, at least 99% pure.

A "compound," as used herein, refers to any type of substance or agent that is commonly considered a drug, therapeutic, pharmaceutical, small molecule, or a candidate for use as the same, as well as combinations and mixtures of the above.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "prevent," as used herein, means to stop something from happening, or taking advance measures against something possible or probable from happening. In the context of medicine, "prevention" generally refers to action taken to decrease the chance of getting a disease or condition.

The term "regulate" refers to either stimulating or inhibiting a function or activity of interest.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

As used herein, the terms "treating," "treatment", and "to treat" are used to indicate the production of beneficial or desired results, such as to alleviate symptoms, or eliminate the causation of a disease or disorder either on a temporary or a permanent basis, slow the appearance of symptoms and/or progression of the disorder, or prevent progression of disease. The terms "treat" or "treatment" refer to both therapeutic treatment and prophylactic or preventative measures, wherein the object is to prevent or slow down the development or spread of disease or symptoms. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also refer to prolonging survival as compared to expected survival if not receiving treatment.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as.

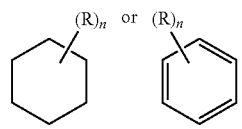

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

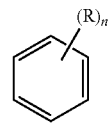

wherein n is an integer from 0 to 2 comprises compound groups including, but not limited to:

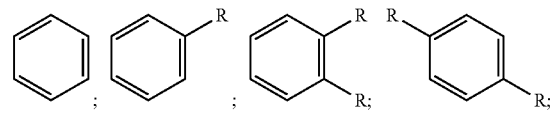

and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "heterocycle" refers to a non-aromatic or aromatic, monocyclic or multicyclic ring system of about 3 to about 14 atoms, wherein at least one of the atoms is a heteroatom (e.g., oxygen, nitrogen, or sulfur). The term "N-heterocycle" refers to a heterocycle wherein at least one of the heteroatoms is a nitrogen atom. Examples of N-heterocycles include, but are not limited to, azetidine, pyrrolidine, pyrrole, pyrroline, piperidine, pyridine, piperazine, pyrazine, pyrimidine, pyridazine, morpholine, and thiazine.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

As used herein, the term "acyl" refers to an organic carboxylic acid group wherein the —OH of the carboxyl group has been replaced with another substituent (i.e., as represented by RC(=O)—, wherein R is an alkyl, substituted alkyl, aralkyl, aryl or substituted aryl group as defined herein). As such, the term "acyl" specifically includes arylacyl groups, such as an acetylfuran and a phenacyl group. Specific examples of acyl groups include acetyl and benzoyl.

"N-acyl" refers to a group having the structure —N—C (=O)—R, wherein R is as defined for acyl. These groups can also be referred to as amides. Modified N-acyl groups include compounds wherein the oxygen of the N-acyl has been replaced by S or NH, as well as to compounds wherein the carbonyl group (i.e., the —C(═O)—) is attached to a second heteroatom in addition to the nitrogen. For example, the carbonyl can be attached to a second nitrogen atom to form a urea linkage (i.e., —NH—C(═O)—NH—R).

The term "amino" refers to the —NH$_2$, the —NHR, and the —NR$_2$ groups, wherein each R is independently alkyl, substituted alkyl, aryl, substituted aryl, or aralkyl, as well as to amino and ammonium functionalities in N-heterocycles (e.g., morpholine, etc). As used herein the term "amino" can also refer to substituents that provide quaternary ammonium cations, such as —$^+$NH$_3$, —$^+$NH(R)$_2$, and —$^+$N(R)$_3$ groups, wherein each R is independently alkyl, substituted alkyl, aryl, substituted aryl or aralkyl.

The term "ester" refers to a moiety comprising an —O—C(═O)—R group, wherein R can be alkyl, substituted alkyl, aralkyl, aryl, or substituted aryl. In some embodiments, the R group can include an amino substituent and the ester is an amino ester.

The term "amide" refers to a moiety comprising a —N(R')—C(═O)—R group, wherein R is selected from alkyl, substituted alkyl, aralkyl, aryl or substituted aryl and R' is H, alkyl, substituted alkyl, aralkyl, aryl, or substituted aryl.

The term "urea" as used herein can refer to a moiety comprising a —N(R')—C(═O)—N(R')— group, wherein each R' is independently H, alkyl, substituted alkyl, aralkyl, aryl, or substituted aryl.

The term "hydroxyl" refers to the —OH group.

When the term "independently selected" is used, the substituents being referred to (e.g., R groups, such as groups R$_1$ and R$_2$, or groups X and Y), can be identical or different. For example, both R$_1$ and R$_2$ can be substituted alkyls, or R$_1$ can be hydrogen and R$_2$ can be a substituted alkyl, and the like.

General Considerations

Chondroitin sulfates (CS or ChS) are sulfated polysaccharides and widely present on the mammalian cell surface and in the extracellular matrix. CS is known to be involved in cancer metastasis, parasitic infections and neuron growth inhibition after injury. The sulfation patterns in CS dictate the binding affinity to the protein targets to manifest the selectivity in biological functions. A 6-O-sulfated N-acetyl galactosamine (GalNAc6S) containing CS facilitates the infection of *B. burgdorferi* to cause lyme disease, and 4-O-sulfated N-acetyl galactosamine (GalNAc4S) involves in *P. falciparum* infection to cause malaria. A domain containing 4,6 disulfated N-acetyl galactosamine (GalNAc4S6S) residues can, in some instances, be necessary to direct neuronal signaling and inhibit axon growth.

Nevertheless, much about CS, its effects on biological systems, and potential as a therapeutic compound remains unknown. This is partially because isolating a polysaccharide with a single sulfated saccharide sequence and defined length is technically demanding. Until now, the lack of structurally homogeneous or monodisperse CS is the major roadblock that hinders CS research, and applications of the same for treatments and therapies.

Disclosed herein are CS compounds and therapeutic compositions comprising CS. Also disclosed herein are therapeutic approaches using CS compounds and compositions, use of CS compounds and compositions for the preparation of medicaments for the treatment for histone toxicity, sepsis and related conditions, and methods of treatment for histone toxicity, sepsis and related conditions using such CS therapeutics.

Various forms of CS are disclosed herein. The uses and methods of treatments disclosed herein include CS compounds comprising sulfated polysaccharides, including those having a size ranging from a trisaccharide to a polysaccharide with nineteen saccharide units, i.e. a 19-mer. CS contains the repeating disaccharide unit of β1→3-linked glucuronic acid (GlcA) and N-acetylgalactosamine (GalNAc) disaccharide, →4)GlcA β(1→3) GalNAcβ(1→Both GlcA and GalNAc residues carry sulfo groups, giving rise to different types of CS. Chondroitin sulfate A (CS-A) contains 4-O-sulfated GalNAc (GalNAc4S) residues, chondroitin sulfate C (CS-C) contains 6-O-sulfated GalNAc (GalNAc6S), chondroitin sulfate D (CS-D) contains 2-O-sulfated GlcA and chondroitin sulfate E (CS-E) contains 4,6-O-disulfated GalNAc. Specialized CS sulfotransferases, including 4-O-sulfotransferase (CS4OST), 6-O-sulfotransferase (CS6OST), 2-O-sulfotransferase and GalNAc4S-6-O-sulfotransferase, participate in the biosynthesis of CS.

In some embodiments, provided herein are methods of treating histone toxicity in a subject. Additionally, in some embodiments, provided herein are methods of treating sepsis or related condition in a subject. Such methods can in some embodiments comprise providing a subject in need of histone toxicity treatment or sepsis treatment, and administering to the subject a chondroitin sulfate compound such that the histone toxicity and/or sepsis in the subject is treated. Such a subject can be suffering from any condition related to or caused by histone toxicity, sepsis, bacterial lipopolysaccharide (LPS) shock, and any related conditions. The subject can be a human subject.

Sepsis occurs when chemicals released in the bloodstream to fight an infection trigger inflammation throughout the body. This can cause a cascade of changes that damage multiple organ systems, leading them to fail, sometimes even resulting in death. Symptoms include, but are not limited to, fever, difficulty breathing, low blood pressure, fast heart rate, and mental confusion.

In some embodiments, the chondroitin sulfate compound can comprise a CS backbone, CS-A, CS-E, CS-C and/or combinations thereof. In some embodiments, the chondroitin sulfate compound can comprise chondroitin sulfate backbone 19 mer, CS-A 19 mer, CS-C 19 mer, CS-E 19 mer, CS backbone 13 mer, CS-A 13 mer, CS-C 13 mer, CS-E 13 mer, backbone 7 mer, CS-A 7 mer, CS-C 7 mer, CS-E 7 mer and/or combinations thereof, and/or any other CS compound synthesizable via the methods and synthesis routes disclosed herein.

The chondroitin sulfate compound can be administered as part of a pharmaceutical composition. In some aspects, the pharmaceutical composition can comprise a CS compound and a pharmaceutically acceptable carrier or adjuvant for administration of the CS compound.

In some aspects, provided herein is a pharmaceutical composition comprising one or more chondroitin sulfate compounds and a pharmaceutically acceptable carrier. In such pharmaceutical compositions the chondroitin sulfate compound can comprise a CS backbone, CS-A, CS-E, CS-C and/or combinations thereof. The chondroitin sulfate compound can comprise a chondroitin sulfate backbone 19 mer, CS-A 19 mer, CS-C 19 mer, CS-E 19 mer, CS backbone 13 mer, CS-A 13 mer, CS-C 13 mer, CS-E 13 mer, backbone 7 mer, CS-A 7 mer, CS-C 7 mer, CS-E 7 mer and/or combinations thereof, and/or any other CS compound synthesizable via the methods and synthesis routes disclosed herein.

Therapeutic Compositions and Methods of Treatment

The presently disclosed subject matter provides pharmaceutical and/or therapeutic compositions comprising a CS compound, as disclosed herein. In some embodiments, a pharmaceutical composition can comprise one or more CS as disclosed herein.

In some embodiments a pharmaceutical composition can also contain a pharmaceutically acceptable carrier or adjuvant for administration of the CS. In some embodiments, the carrier is pharmaceutically acceptable for use in humans. The carrier or adjuvant desirably should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated for administration to the patient.

Suitable formulations of pharmaceutical compositions of the presently disclosed subject matter include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the presently disclosed subject matter can have a pH between 5.5 and 8.5, preferably between 6 and 8, and more preferably about 7. The pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

Therapeutic uses and/or methods and/or methods of treatment are also provided herein. A therapeutic method according to the presently disclosed subject matter comprises administering to a subject in need thereof a CS or related compound as disclosed herein. A use according to the presently disclosed subject matter comprises use of a CS or related compound as disclosed herein for the preparation of a medicament for a therapeutic indication as disclosed herein.

An effective dose of a pharmaceutical composition of the presently disclosed subject matter is administered to a subject in need thereof. The terms "therapeutically effective amount", "therapeutically effective dose", "effective amount", "effective dose" and variations thereof are used interchangeably herein and refer to an amount of a therapeutic composition or pharmaceutical composition of the presently disclosed subject matter sufficient to produce a measurable response (e.g. reduced symptoms of sepsis). Actual dosage levels can be varied so as to administer an amount that is effective to achieve the desired therapeutic response for a particular subject.

In some embodiments, the quantity of a therapeutic composition of the presently disclosed subject matter administered to a subject will depend on a number of factors including but not limited to the subject's size, weight, age, the target tissue or organ, the route of administration, the condition to be treated, and the severity of the condition to be treated.

The potency of a therapeutic composition can vary, and therefore a "therapeutically effective" amount can vary. However, using the assay methods described herein below, one skilled in the art can readily assess the potency and efficacy of the pharmaceutical compositions of the presently disclosed subject matter and adjust the therapeutic regimen accordingly.

In some aspects, provided herein are pharmaceutical composition for use in treating histone toxicity and/or sepsis, the composition comprising one or more chondroitin sulfate compounds and a pharmaceutically acceptable carrier. In some embodiments, the chondroitin sulfate compound in such uses can comprise a CS backbone, CS-A, CS-E, CS-C and/or combinations thereof. In some embodiments, the chondroitin sulfate compound in such uses can comprise chondroitin sulfate backbone 19 mer, CS-A 19 mer, CS-C 19 mer, CS-E 19 mer, CS backbone 13 mer, CS-A 13 mer, CS-C 13 mer, CS-E 13 mer and/or combinations thereof.

Subjects

The subject treated in the presently disclosed subject matter is desirably a human subject, although it is to be understood that the principles of the disclosed subject matter indicate that the compositions and methods are effective with respect to invertebrate and to all vertebrate species, including mammals, which are intended to be included in the term "subject". Moreover, a mammal is understood to include any mammalian species in which treatment of histone toxicity conditions is desirable, particularly agricultural and domestic mammalian species.

The methods of the presently disclosed subject matter are particularly useful in the treatment of warm-blooded vertebrates. Thus, the presently disclosed subject matter concerns mammals and birds.

More particularly, provided herein is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided herein is the treatment of livestock, including, but not limited to, domesticated swine (pigs and hogs), ruminants, horses, poultry, and the like.

CS Compounds

In development of the disclosed methods of CS synthesis significant challenges were overcome, including for example improving the accessibility of recombinant CS biosynthetic enzymes and reducing the production cost for UDP-GalNAc. In addition to synthesizing natural CS oligosaccharides, the instant disclosure provides for the possibility of preparing unnatural 6-O-sulfated CS oligosaccharides. The synthesis was accomplished in multi-milligram scales, allowing complete structural characterization by MS and NMR. In addition to CS-A and CS-C and CS-E were also synthesized by methods disclosed herein. The demonstration of the enzymatic synthesis of structurally defined CS oligosaccharides offers an essential tool to investigate the biological functions of CS.

In addition to the CS compounds ranging from trisaccharides to nonasaccharides, i.e. 9-mers, as shown in FIG. 2B and herein, the disclosed methods provide for the synthesis of larger and/or longer CS compounds, as shown in FIG. 2A, and below. Further details of CS synthesis can be found in International Patent Application Publication No. WO 2019/010216, herein incorporated by reference in its entirety.

Example CS-A Oligosaccharides (11-Mer to 19-Mer)

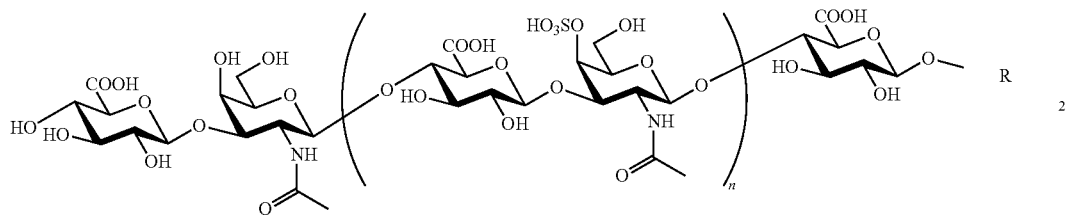

n=4, CS-A 11-mer
n=5, CS-A 13-mer
n=6, CS-A 15-mer
n=7, CS-A 17-mer
n=8, CS-A 19-mer, wherein R is selected from the group consisting of —H, alkyl (such as but not limited to —$CH_3$ or —$CH_2CH_3$), substituted alkyl, aryl, and substituted aryl (such as but not limited to a p-nitrophenyl group).

Example CS-C Oligosaccharides (11-Mer to 19-Mer)

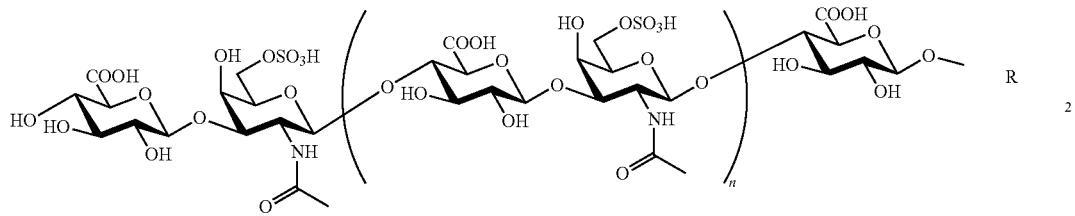

n=4, CS-C 11-mer
n=5, CS-C 13-mer
n=6, CS-C 15-mer
n=7, CS-C 17-mer
n=8, CS-C 19-mer, wherein R is selected from the group consisting of —H, alkyl (such as but not limited to —$CH_3$ or —$CH_2CH_3$), substituted alkyl, aryl, and substituted aryl (such as but not limited to a p-nitrophenyl group).

Example CS-E Oligosaccharides (5-Mer to 19-Mer)

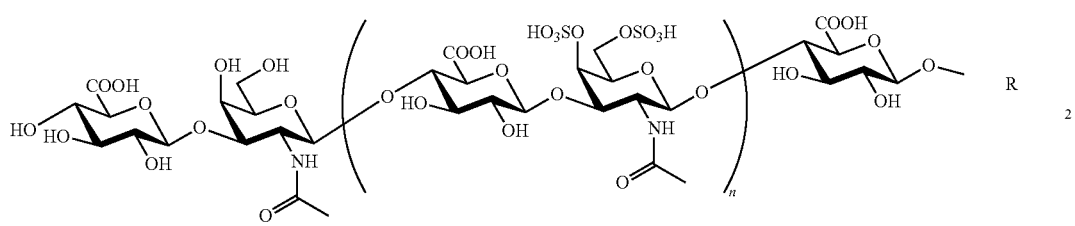

n=1, CS-E 5-mer
n=2, CS-E 7-mer
n=3, CS-E 9-mer
n=4, CS-E 11-mer
n=5, CS-E 13-mer
n=6, CS-E 15-mer
n=7, CS-E 17-mer
n=8, CS-E 19-mer, wherein R is selected from the group consisting of —H, alkyl (such as but not limited to —$CH_3$ or —$CH_2CH_3$), substituted alkyl, aryl, and substituted aryl (such as but not limited to a p-nitrophenyl group).

Approaches for synthesizing CS-E were developed as disclosed herein. Such methods utilize similar approaches as with the synthesis of CS-A and CS-C, but with additional enzymatic steps. For example, in some embodiments the synthesis of CS-E requires additional CS sulfotransferases, including for example GalNAc4S-6-O-sulfotransferase. The instant disclosure provides both 2-O-sulfotransferase and GalNAc4S-6-O-sulfotransferase needed for such additional steps.

CS compounds as disclosed herein can also be illustrated as shown below:

Chemical Structures CS and CS-A Oligosaccharides:

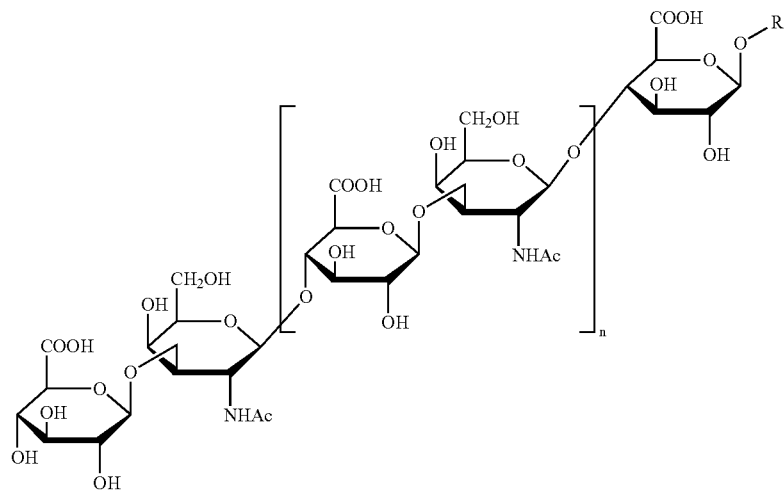

n=2, CS 7-mer
n=5, CS 13-mer
n=8, CS 19-mer wherein R is selected from the group consisting of —H, alkyl (such as but not limited to —$CH_3$ or —$CH_2CH_3$), substituted alkyl, aryl, and substituted aryl (such as but not limited to a p-nitrophenyl group) $NO_2$ In some embodiments, R is

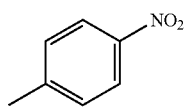

n=2, CS-A 7-mer
n=5, CS-A 13-mer
n=8, CS-A 19-mer wherein R is selected from the group consisting of —H, alkyl (such as but not limited to —$CH_3$ or —$CH_2CH_3$), substituted alkyl, aryl, and substituted aryl (such as but not limited to a p-nitrophenyl group).

In some embodiments, R is

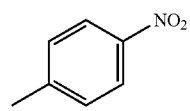

Chemical Structures of CS-C and CS-E Oligosaccharides

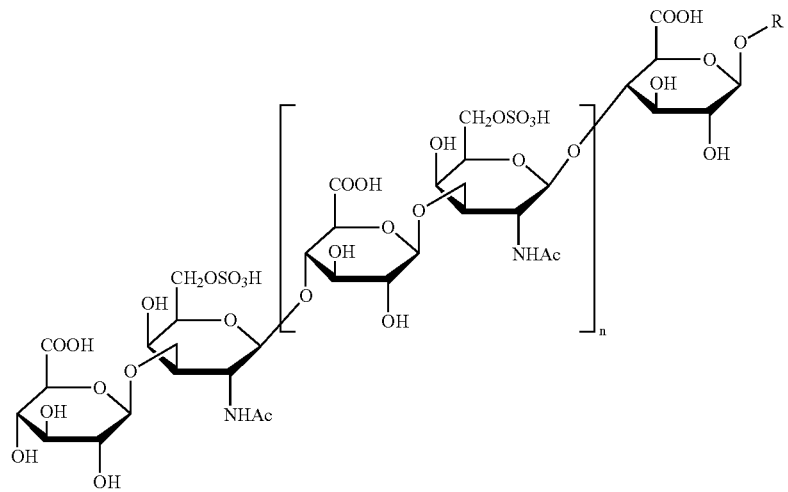

n=2, CS-C 7-mer
n=5, CS-C 13-mer
n=8, CS-C 19-mer wherein R is selected from the group consisting of —H, alkyl (such as but not limited to —CH$_3$ or —CH$_2$CH$_3$), substituted alkyl, aryl, and substituted aryl (such as but not limited to a p-nitrophenyl group).

In some embodiments, R is

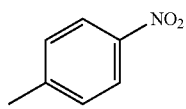

n=2, CS-E 7-mer
n=5, CS-E 13-mer
n=8, CS-E 19-mer wherein R is selected from the group consisting of —H, alkyl (such as but not limited to —CH$_3$ or —CH$_2$CH$_3$), substituted alkyl, aryl, and substituted aryl (such as but not limited to a p-nitrophenyl group).

In some embodiments, R is

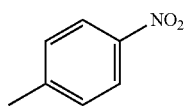

EXAMPLES

The present disclosure will now be described with reference to the following examples. It should be appreciated that these examples are not intended to limit the scope of the claims to the present disclosure, but are rather intended to be exemplary of certain embodiments. Any variations in the exemplified methods that occur to the skilled artisan are intended to fall within the scope of the present disclosure.

Example 1

CS Mitigation of Histone-Induced Endothelial Cytotoxicity

The human endothelial cell line EA.hy926 cells (ATCC) were cultured in Dulbecco's modified Eagle medium (DMEM, Gibco) supplemented with 10% fetal bovine serum and 1% penicillin-streptomycin (Gibco) at 37° C. and 5% CO$_2$. For experiments, 5×10$^5$ cells were plated in 12-well plates (Corning) and incubated overnight, then washed with serum-free DMEM. EA.hy926 were treated with 30 µg/mL calf thymus histones (Roche) in the presence of the following compounds: chondroitin sulphate (CS) backbone 19 mer, CS A 19 mer, CS C 19 mer, CS E 19 mer, CS backbone 13 mer, CS A 13 mer, CS C 13 mer or CS E 13 mer. The structures of each are provided herein. The endothelial cells were exposed to the treatments for 1 hour at 37° C. and 5% CO$_2$. Medium was removed and cells were detached from the plate with 0.05% Trypsin-EDTA (Gibco). Cells were washed with PBS and centrifuged at 500 g, then resuspended in PBS (Gibco). To measure cell death, cells were incubated with 10 µg/mL propidium iodide (PI, Sigma) for 10 minutes at room temperature. PI is a cell-impermeable fluorescent dye that is excluded from viable cells and taken up into necrotic cells, where it binds to double stranded DNA between base pairs. PI positive cells were detected by flow cytometry with excitation at 488 nm and emission detection at 617 nm. Data are represented as percent of total cells that were PI positive.

The results of the experiments of Example 1 are shown in FIG. 1A. More particularly, the results demonstrate that in some embodiments, using the cell based assay model, the synthesized CS oligosaccharides can neutralize histone cellular toxic.

Example 2

CS Mitigation of Histone-Induced Mortality

Male C57Bl6/J mice (Jackson Laboratories) were housed at the University of North Carolina (Chapel Hill, N.C., United States of America) in a 12-hour light-dark cycle with food and water ad libitum for one week. This study was performed according to a protocol approved by the University of North Carolina Institutional Animal Care and Use Committee. Mice were intravenously injected with sterile saline (n=8) or 75 mg/kg ChS E 19 mer (n=5) followed 1 minute later by calf thymus histones (75 mg/kg). Seven of the 8 mice that received histones alone (saline treatment) died within 15 minutes of infusion, likely from cardiac arrest. All five of the mice that received ChS E 19 mer survived. The ratio of ChS E 19 mer to calf thymus histones was 3:1, which is less than used in the in vitro endothelial cytotprotection (where the ratio was 10:1).

The results of the experiments of Example 2 are shown in FIG. 1B. More particularly, the results demonstrate that the survival rate of the mice treated by histone together with CS oligosaccharides had a survival rate of 100%, whereas none of the mice exposed to histones and receiving no CS therapy survived. Kaplan-Meier survival curves by log-rank test using GraphPad Prism software was performed to obtained P=0.001

Example 3

Synthesis of CS Compounds

Based on the effectiveness of CS in mitigating histone-induced endothelial toxicity and mortality, as set forth in Examples 1 and 2, further studies were conducted to characterize CS compounds and elucidate their functionality.

Histones are DNA-binding proteins are encapsulated inside nuclei. Release of histones are associated with neutrophil activation in responding to infection or inflammation stimulations (1, 2). Extracellular histones exhibit cytotoxicity towards the host, which contributes to disease states, including sepsis (3). Histones contain isoforms, and histone H3 is the predominant form that is attributed to the cytotoxicity (4).

CS-E isolated from human tissue or maritime organisms are a mixture of polysaccharides with different sizes and sulfation patterns, making the study for the structure and activity relationship difficult. What is needed is the ability to enzymatically synthesize homogeneous CS-E oligosaccharides. The synthesis of CS-E oligosaccharides was initiated from a commercially available monosaccharide, p-nitrophenyl glucuronide (GlcA-pNP)(FIG. 2A). The synthesis involved the elongation of the monosaccharide to the desired size using a bacterial glycosyltransferase (KfoC) to form nonsulfated chondroitin backbone. The backbone underwent two rounds of sulfotransferase modifications. Sulfation with chondroitin sulfate 4-O-sulfotransferase (CS 4OST) was performed to form chondroitin sulfate A (CS-A) oligosaccharides. Then, modification by 4-O-sulfo GalNAc 6-O-sulfotransferase (GalNAc4S-6OST) to form 4,6-disulfated GalNAc residue was followed to obtain CS-E products. The access of highly active GalNAc4S-6OST was critically important for the synthesis of CS-E oligosaccharides. A high level expression of GalNAc4S-6OST was achieved in insect cells using the baculovirus expression approach. Baculovirus contains an endogenous chondroitinase that may cleave CS substrates (6). Therefore, it is imperative to purify GalNAc4S-6OST away from the viral endogenous chondroitinase for the synthesis purpose. Using the enzymatic approach, three CS-E oligosaccharides, namely CS-E 7-mer, CS-E 13-mer, and CS-E 19-mer, were obtained in the scale of 10 to 100 mg. A nonsulfated chondroitin nonadecasaccharide backbone, CS-0S 19-mer, was also synthesized to serve as a control oligosaccharide for the subsequent biological studies. See FIG. 2B.

Example 4

Characterization of the Structure of CS Compounds

The CS-E oligosaccharides were analyzed using high resolution diethylaminoethyl (DEAE)-HPLC, high resolution mass spectrometry, and NMR spectroscopy. As a representative example, CS-E 7-mer was eluted a single symmetric peak, demonstrating its high purity (FIG. 3A). High resolution mass spectrometry analysis revealed its molecular mass to be 1772.227, which is very close to the calculated value of 1772.221 (FIG. 3B). $^1$H-NMR and $^{13}$C-NMR analysis also confirmed the purity of CS-E 7-mer. Additional NMR analyses were employed to determine the site of sulfation and the nature of glycosidic linkages between GalNAc and GlcA. CS-E 13-mer and CS-E 19-mer contain multiple copies of repeating disaccharide units of -GalNAc4S6S-GlcA-, causing substantial overlaps in the NMR signals. Therefore, their structures were primarily determined based on the molecular mass measurement by high resolution mass spectrometry.

Example 5

Characterization of the Activity of CS Compounds

The availability of long CS-E oligosaccharides opened up new opportunities to investigate the biological functions of CS. The anti-inflammatory effects of homogeneous CS-E oligosaccharides was sought to be exploited by targeting to histones. Histones are positively charged proteins that bind to DNA and are encapsulated inside nuclei under healthy conditions. When histones are released by pathological stimuli, the extracellular histones display potent cytotoxicity. Targeting to extracellular histone is a possible strategy to treat inflammatory diseases. As such, it was hypothesized that CS oligosaccharides bind to histone and neutralize the cytotoxicity. The binding affinity ($K_D$) measurement indicated that CS-E 19-mer binds tightly to histone H3 (44.7 nM), and the binding affinity generally decreases as the sizes of oligosaccharides shorten (Table 1).

TABLE 1

Summary of kinetic data of H3 histone binding to CSE oligo interactions*

| Interactions | $k_a$ (1/MS) | $k_d$ (1/S) | $K_D$ (M) |
|---|---|---|---|
| CS-E 7-mer | No binding | No binding | — |
| CS-E 13-mer | 7.65 × 10$^5$ | 0.124 | 1.62 × 10$^{-7}$ |
|  | (±3.37 × 10$^4$) | (±3.14 × 10$^{-3}$) |  |
| CS-E 19mer | 9.55 × 10$^5$ | 0.0426 | 4.47 × 10$^{-8}$ |
|  | (±6.29 × 10$^4$) | (±1.70 × 10$^{-3}$) |  |
| CS-0S 19-mer | No binding | no binding |  |

*The data with (±) in parentheses are the standard deviations (SD) from global fitting of four or five injections.

Sulfation also contributes to the binding affinity to histone H3. CS-0S 19-mer, a nonsulfated chondroitin backbone, did not bind to histone H3. The binding affinities of different CS-E oligosaccharides towards a mixture of histone isoforms were also determined, showing a similar trend as the oligosaccharides bind to histone H3. See Table 2.

TABLE 2

Summary of kinetic data of histone mixture binding to CSE oligo interactions*

| Interactions | $k_a$ (1/MS) | $k_d$ (1/S) | $K_D$ (M) |
|---|---|---|---|
| CS-E 7-mer | No binding | No binding | |
| CS-E 13mer | $5.92 \times 10^5$ ($\pm 1.58 \times 10^4$) | 0.141 ($\pm 3.01 \times 10^{-3}$) | $2.38 \times 10^{-7}$ |
| CS-E 19mer | $9.8 \times 10^5$ ($\pm 6.00 \times 10^{4)}$) | 0.0704 ($\pm 2.28 \times 10^{-3}$) | $7.17 \times 10^{-8}$ |
| CS-0S 19-mer | No binding | no binding | |

*The data with (±) in parentheses are the standard deviations (SD) from global fitting of four or five injections.

Example 6

Further Evaluation of CS Mitigation of Histone-Induced Toxicity and Morbidity Administration of histones is known to be toxic to mice (4). As noted above, it was demonstrated that CS-E 19-mer protects against histone-mediated animal death (FIG. 1B). Five out of six (83.3%) animals died within 60 min after administering histone (75 mg/kg), whereas, treatment with CS-E 19-mer (75 mg/kg) among histone-intoxicated mice, all five mice (100%) survived during the course of the experiment. The damages to lung tissue were also examined with or without the treatment with CS-E 19-mer. H&E staining of the lung tissue from histone-treated mice demonstrated the massive formation of thrombosis inside and outside blood vessels (FIG. 4A). Data suggest that administration of histones not only induced blood clot formation inside blood vessel but also caused vascular leakage to lead to blood clot outside blood vessel. A notable reduction in blood clot in the lung from the mice receiving CS-E 19-mer was observed (FIG. 4A). The thrombosis was also found in liver and kidney in the histone-treated mice. Likewise, CS-E 19-mer is able to reduce the thrombosis in liver and kidney as well (FIG. 4B). Taking together, these data suggest that CS-E 19-mer binds to histones and effectively protects against histones' toxic effects in organ damages in mice.

Example 7

Evaluation of the Protective Effect of CS Against Bacterial Lipopolysaccharide (LPS) Shock Next, the protective effect of CS-E 19-mer against bacterial lipopolysaccharide (LPS) shock was examined. LPS rich in the cell wall of gram-negative bacteria, also known as endotoxin, induce exuberated inflammatory responses in the host, leading to life-threatening sepsis-like symptoms that causes >750,000 deaths per year in US. One mechanism from LPS-caused death is because LPS induces the release of cytotoxic extracellular histones (7). As expected, administration of LPS to mice led to the release of histone H3 in plasma (FIG. 5A). Furthermore, administration of LPS (6 mg/kg) caused 85% mice die in 72 hours; whereas, the treatment of CS-E 19-mer (0.5 mg/kg) reduced the death rate to 30%, suggesting that CS-E 19-mer displays protective effect against LSP-induced death (FIG. 5B). Biomarkers were also measured to assess the organ damage and to substantiate CS-E 19-mer's functions. A significant reduction in blood urine nitrogen (BUN) level was detected, a marker for kidney function (FIG. 5C). We also observed reduction in the level of creatinine after CS-E 19-mer treatment, a marker for kidney function (FIG. 5D). Although the reduction in creatinine is trending towards statistically significant, the combination of this data with reduction of BUN level allowed us to confirm that CS-E 19-mer displays the protective effect against kidney damage induced by LPS. The plasma level of asparate aminotransferase (AST), a marker for liver damage, was also reduced in the CS-E 19-mer treated group, suggesting that the compound protects the liver damage caused by LPS (FIG. 5E). Overall, CS-E 19-mer protects organ damage caused by LPS and increases survival rate in mice after exposing to LPS.

Three lines of evidence suggest that the protective effect of CS-E 19-mer against LPS-induced organ damage are attributed to its ability to neutralize histone and protect the damage of endothelial cells caused by histone. First, it was demonstrated that CS-E 19-mer is able to pull down histone H3 from mice plasma (FIG. 6A). To this end, LPS-treated mice plasma was incubated with biotinylated CS-E 19-mer followed by affinity purification using an avidin-agarose column. Histone H3 was detected in the plasma sample after CS-E 19-mer affinity purification (FIG. 6A, lane 5). The result from this experiment suggests that CS-E 19-mer forms complex with histones under in vivo conditions, and the binding neutralizes the toxicity of histones. Second, the protective effect of CS-E 19-mer against endothelia cell death caused by histone was evaluated. EA.hy926 cells were treated with histone H3, and the cell death was measured using flow cytometry based on PI staining (7). Addition of CS-E 19-mer lowered the cell death in a dose responsive manner (FIG. 6B). Smaller degree protection was observed for CS-E 13-mer, consistent with the observation that it displays lower binding affinity to histones than CS-E 19-mer. No protective effect was observed for CS-0S 19-mer. Third, administration of CS-E 19-mer protects against the vascular leakage induced by LPS, whereas the reduction by CS-E 19-mer in kidney is less significant, and there was no significant effect on reducing the vascular permeability in the liver (FIGS. 6C-6E).

Example 8

Conclusions Based on Studies of CS Compounds and Uses of Same

The flexible and effective synthesis methods and approaches for CS compounds as disclosed herein was demonstrated through synthesizing numerous CS compounds, including for example CS-E oligosaccharides in different sizes, such as for example 5-mer, 9-mer, 11-mer, 15-mer and 17-mer. For clarity and simplicity, the present studies focused on CS-E 7-mer, CS-E 13-mer and CS-E 19-mer, but the results and application are not limited thereto. It should be noted that bikunin, the simplest CS proteoglycan isolated from natural sources, has a size of about 27 to about 39 saccharide residues (8). The size of 19-mer CS oligosaccharides synthesized and disclosed herein is about 50% to about 70% of full-length CS chain from nature.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

1. Brinkmann V, Reichard U, Goosmann C, Fauler B, Uhlemann Y, Weiss D S, et al. Neutrophil extracellular traps kill bacteria. *Science*. 2004; 303:1532-5.
2. Clark S R, Ma A C, Tavener S A, McDonald B, Goodarzi Z, Kelly M M, et al. Platelet TLR4 activates neutrophil extracellular traps to ensnare bacteria in septic blood. *Nat Med*. 2007; 13:463-9.
3. Wildhagen K C, Garcia de Frutos P, Reutelingsperger C P, Schrijver R, Areste C, Ortega-Gomez A, et al. Nonanticoagulant heparin prevents histone-mediated cytotoxicity in vitro and improves survival in sepsis. *Blood*. 2014; 123:1098-101.
4. Xu J, Zhang X, Pelayo R, Monestier M, Ammollo C T, Semeraro F, et al. Extracellular histones are major mediators of death in sepsis. *Nat Med*. 2009; 15:1318-21.
5. Li J, Su W, and Liu J. Enzymatic synthesis of homogeneous chondroitin sulfate oligosaccharides. *Angew Chem Int Ed*. 2017; 56:11784-7.
6. Sugiura N, Setoyama y, Chiba M, Kimata K, and Watanabe H. Baculovirus envelope protein ODV-E66 is a novel chondroitinase with distinct substrate specificity. *J Biol Chem*. 2011; 286:29026-34.
7. Xu J, Zhang X, Monestier M, Esmon N L, and Esmon C T. Extracellular histones are mediators of death through TLR2 and TLR4 in mouse fatal liver injury. *J Immunol*. 2011; 187:2626-31.
8. Ly M, Leach III F E, Laremore T N, Toida T, Amster U, and Linhardt R J. The proteoglycan bikunin has sequence. *Nat Chem Biol*. 2011; 7:827-33.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of treating histone toxicity in a subject, the method comprising:
   providing a subject in need of histone toxicity treatment; and
   administering to the subject a chondroitin sulfate (CS) compound,
   wherein the chondroitin sulfate compound comprises a CS backbone, CS-A, CS-E, CS-C and/or combinations thereof, and
   wherein the chondroitin sulfate compound comprises chondroitin sulfate backbone 19 mer, CS-A 19 mer, CS-C 19 mer, CS-E 19 mer, CS backbone 13 mer, CS-A 13 mer, CS-C 13 mer, CS-E 13 mer and/or combinations thereof, and
   wherein the histone toxicity in the subject is treated.

2. The method of claim 1, wherein the subject is suffering from sepsis.

3. The method of claim 1, wherein the subject is a human subject.

4. The method of claim 1, wherein the chondroitin sulfate compound comprises one or more of the following structures:

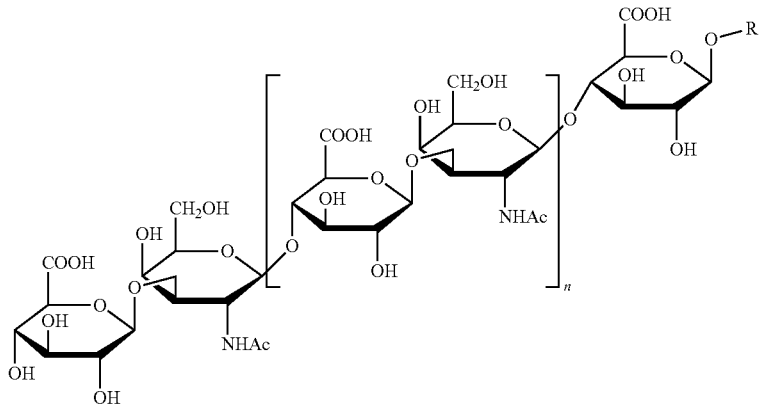

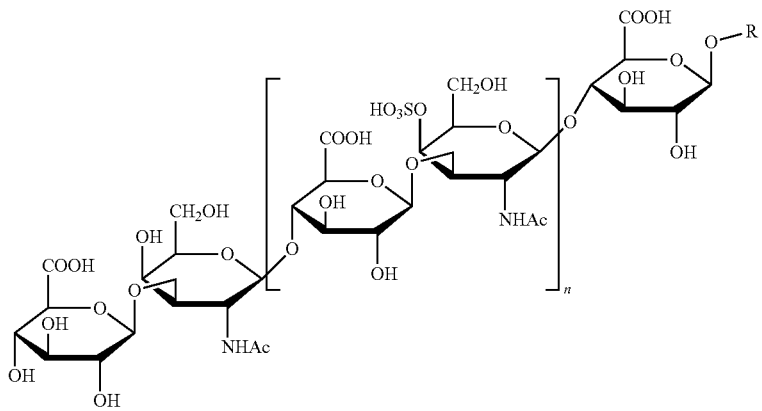

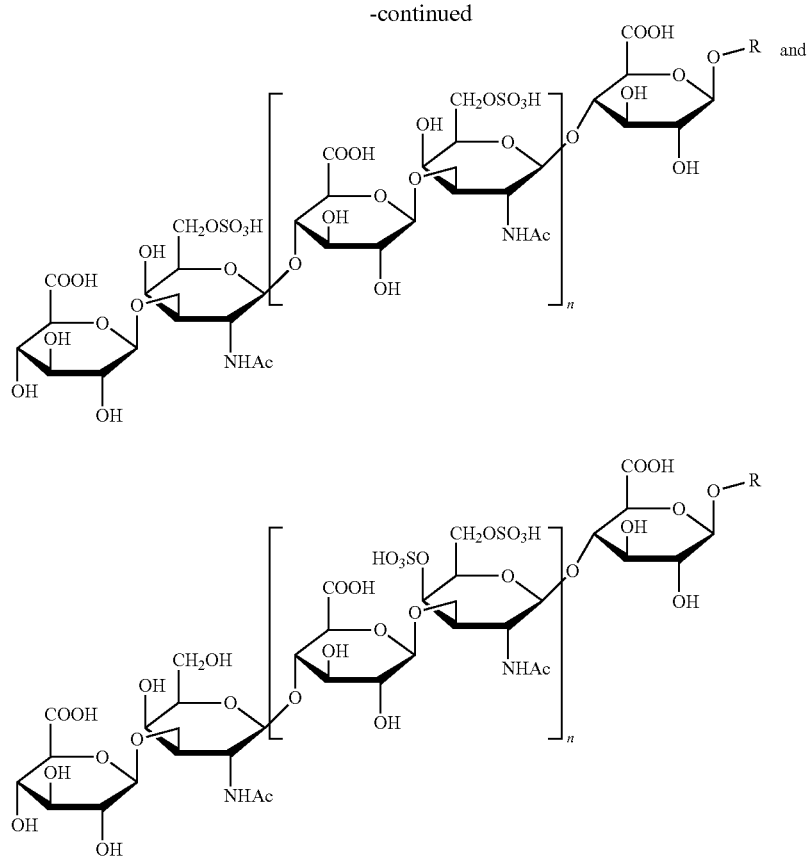

wherein R is selected from the group consisting of —H, alkyl, substituted alkyl, aryl, and substituted aryl, wherein n is 1, 2, 3, 4, 5, 6, 7 or 8.

5. The method of claim 1, wherein the chondroitin sulfate compound is administered as part of a pharmaceutical composition.

6. The method of claim 1, wherein the pharmaceutical composition comprises a CS compound and a pharmaceutically acceptable carrier or adjuvant for administration of the CS.

7. A method of treating sepsis in a subject, the method comprising:
providing a subject in need of sepsis treatment; and
administering to the subject a chondroitin sulfate compound, wherein the chondroitin sulfate compound comprises a CS backbone, CS-A, CS-E, CS-C and/or combinations thereof, and
wherein the chondroitin sulfate compound comprises chondroitin sulfate backbone 19 mer, CS-A 19 mer, CS-C 19 mer, CS-E 19 mer, CS backbone 13 mer, CS-A 13 mer, CS-C 13 mer, CS-E 13 mer and/or combinations thereof wherein the sepsis in the subject is treated.

8. The method of claim 7, wherein the subject is a human subject.

9. The method of claim 7, wherein the chondroitin sulfate compound comprises one or more of the following structures:

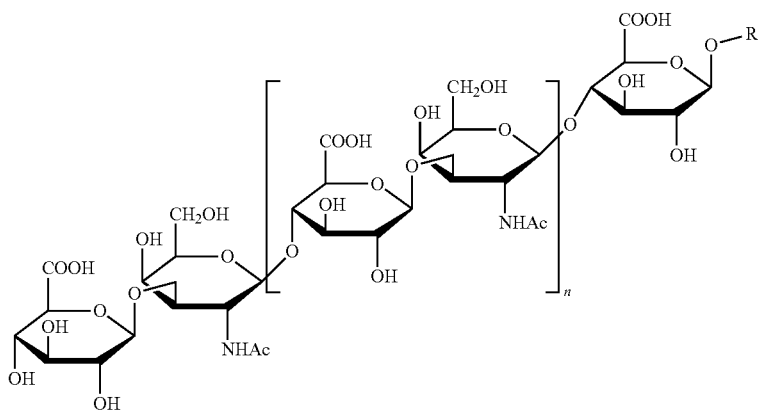

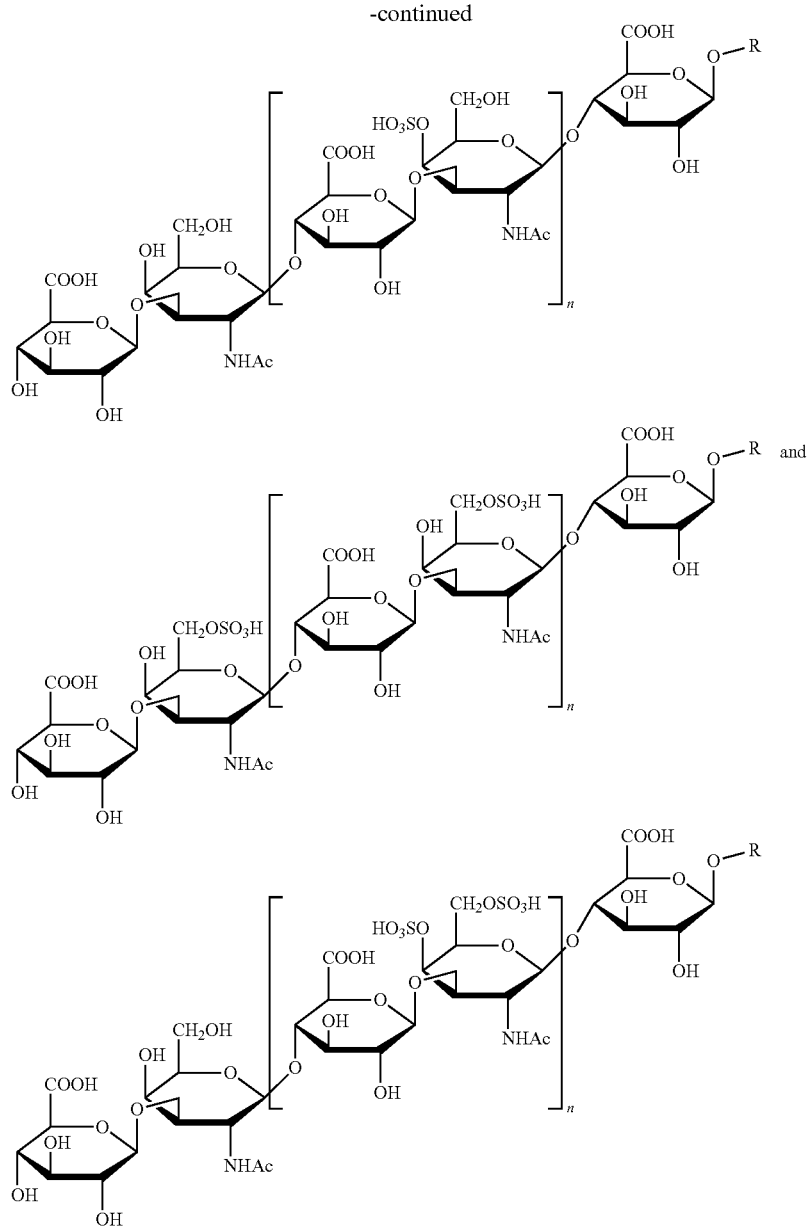

wherein R is selected from the group consisting of —H, alkyl, substituted alkyl, aryl, and substituted aryl, wherein n is 1, 2, 3, 4, 5, 6, 7 or 8.

10. The method of claim 7, wherein the chondroitin sulfate compound is administered as part of a pharmaceutical composition.

11. The method of claim 7, wherein the pharmaceutical composition comprises a CS compound and a pharmaceutically acceptable carrier or adjuvant for administration of the CS.

12. The method of claim 4, wherein the alkyl is —CH$_3$ or —CH$_2$CH$_3$ or the substituted aryl is a p-nitrophenyl group.

13. The method of claim 9, wherein the alkyl is —CH$_3$ or —CH$_2$CH$_3$ or the substituted aryl is a p-nitrophenyl group.

* * * * *